(12) United States Patent
Augustyniak et al.

(10) Patent No.: US 9,645,106 B2
(45) Date of Patent: May 9, 2017

(54) MONOLITHICALLY INTEGRATED HYBRIDISATION SENSOR ASSEMBLY AND ASSOCIATED PRODUCTION METHOD

(75) Inventors: Marcin Augustyniak, München (DE); Christian Paulus, Weilheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 1449 days.

(21) Appl. No.: 11/630,964

(22) PCT Filed: Jun. 27, 2005

(86) PCT No.: PCT/DE2005/001139
§ 371 (c)(1),
(2), (4) Date: Dec. 28, 2006

(87) PCT Pub. No.: WO2006/000204
PCT Pub. Date: Jan. 5, 2006

(65) Prior Publication Data
US 2007/0236224 A1    Oct. 11, 2007

(30) Foreign Application Priority Data
Jun. 29, 2004  (DE) .................. 10 2004 031 371

(51) Int. Cl.
*G01N 27/42*   (2006.01)
*G01N 27/327*  (2006.01)

(52) U.S. Cl.
CPC ................. *G01N 27/3276* (2013.01)

(58) Field of Classification Search
CPC ........... G01N 27/3276; G01N 33/5438; C12Q 1/6834; A61B 5/14865; A61B 5/0031
(Continued)

(56) References Cited

U.S. PATENT DOCUMENTS 6,512,939 B1 *  1/2003  Colvin et al. .................. 600/347
6,885,883 B2 *  4/2005  Parris et al. .................... 600/347
(Continued)

FOREIGN PATENT DOCUMENTS

DE         100 58 397 A1    6/2002
DE         10112778 A1     10/2002
(Continued)

OTHER PUBLICATIONS

U. Tietze, C. Schenk, "Halbleiter-Schaltungstechnik", 11. Auflage, 1999, pp. 954-955.
(Continued)

*Primary Examiner* — William H Beisner
*Assistant Examiner* — Danielle Henkel
(74) *Attorney, Agent, or Firm* — David S. Safran

(57) ABSTRACT

A monolithically integrated sensor assembly is for detecting molecules that are potentially contained in an analyte. The assembly includes: a substrate; at least one sensor electrode, which is located on or in the substrate and is coated with a sensor-active layer, on which electrochemically active particles are generated in the present of the molecules to be detected, the particles being detected via an electric sensor signal on the sensor electrode(s); at least one additional electrode that is located on or in the substrate; and an operating circuit that is integrated into the substrate for controlling the sensor electrode and the additional electrode(s).

24 Claims, 14 Drawing Sheets

(58) Field of Classification Search
USPC .................................................. 435/6, 287.2
See application file for complete search history.

(56) References Cited

U.S. PATENT DOCUMENTS

| | | |
|---|---|---|
| 2004/0063152 A1 | 4/2004 | Gumbrecht et al. |
| 2004/0072223 A1 | 4/2004 | Luyken et al. |
| 2004/0152091 A1 | 8/2004 | Paulus et al. |
| 2005/0136423 A1 | 6/2005 | Paulus et al. |

FOREIGN PATENT DOCUMENTS

| | | |
|---|---|---|
| WO | WO 02/097413 A2 | 12/2002 |
| WO | WO 03/046209 A2 | 6/2003 |

OTHER PUBLICATIONS

A. Bard, L. R. Faulkner, "Electrochemical Methods—Fundamentals and Applications", 1980, Chapter 13.2.3.

M. Paeschke et al., "Voltametric Multichannel Measurements Using Silicon Fabricated Microelectrode Arrays", Electroanalysis, vol. 8, No. 10, 1996, pp. 891-898, ISSN: 1040-0397.

R. Hintsche et al., "Microsbiosensors using electrodes made in Si-technology", Frontiers in Biosensorics I, Fundamental Aspects, 1997, pp. 267-283.

R. Hintsche et al., "Microelectrode arrays and application to biosensing devices", Biosensors & Bioelectronics, vol. 9, 1994, pp. 697-705.

R. Thewes et al., "Sensor Arrays for Fully-Electronic DNA Detection on CMOS", ISSCC 2002, Session 21, TD: Sensors and Microsystems, 21.2.

G. Hartwich, H. Wieder, "DNA-Chips mit direkter elektrischer Detektion der Hybridisierung", Electronenübertragung in Chemie und Biochemie, GdCh-Monographie 23, 2002, ISBN: 3-936028-03-6 (Summary in English).

C. Paulus et al., "A fully Integrated CMOS Sensor System for Chronocoulometry", Proceedings of IEEE Sensors 2003, Bd. 2, pp. 1329-1332, ISBN: 0-7803-8133-5.

M. Schlenle et al., "A Fully Electronic DNA Sensor with 128 Positions and In-Pixel A/D Conversion", IEEE International Solid-State Circuits Conference, Bd. 1, Feb. 2004, vol. 1, 12.2, ISBN: 0-7803-8267-6.

P. Hofmann et al., "Passive DNA Sensor with Gold Electrodes Fabricated in a CMOS Backend Process", ESSDERC 2002, pp. 487-490.

www.combimatrix.com: "DNA Microarrays" paper found on Nov. 17, 2006 under www.combimatrix.com/tech-microarrays.htm.

www.frizbiochem.com: "EDDA—Technology", paper found Nov. 17, 2006 under http://www.frizbiochem.com/cms/de/technology.html.

Paulus et al., "A Fully Integrated CMOS Sensor System for Chronocoulometry" Proceedings of IEEE Sensors 2003, vol. 2, 2003.

* cited by examiner

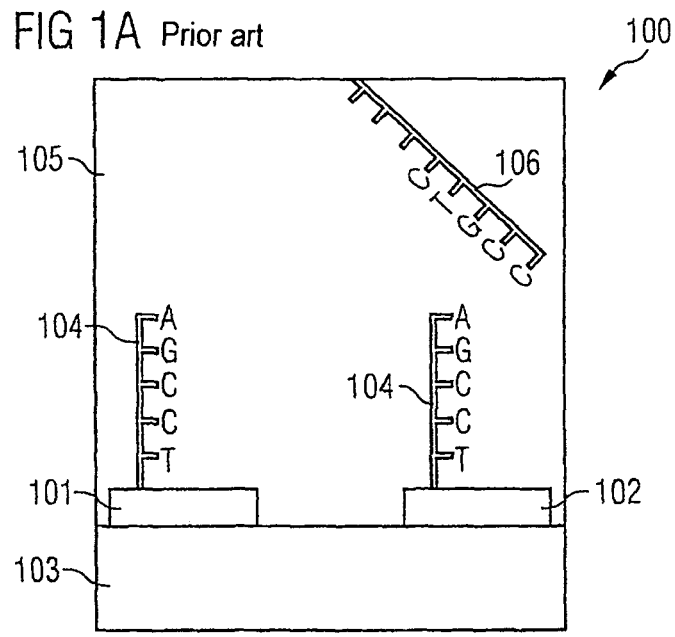
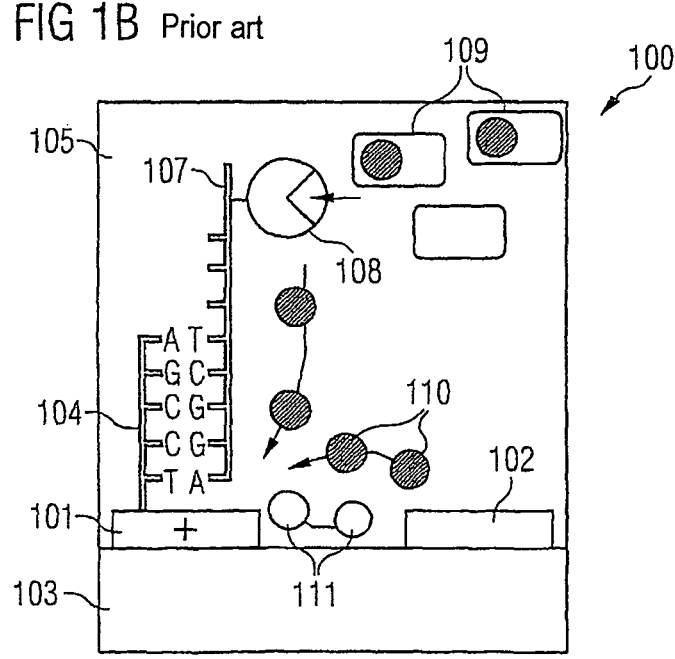

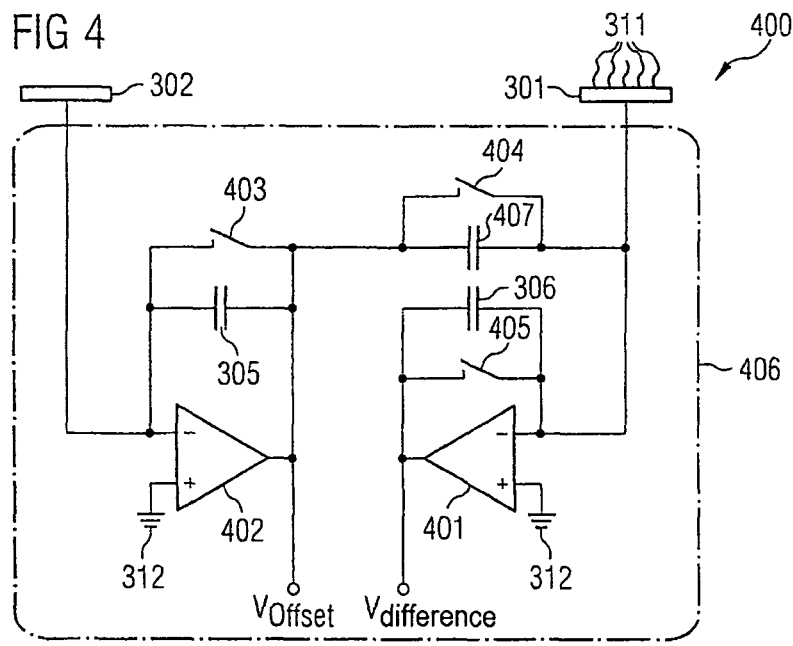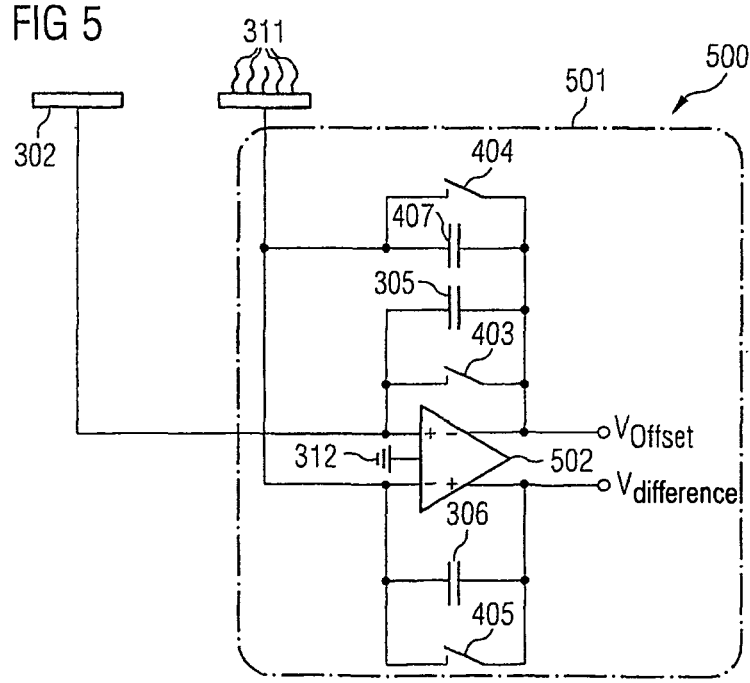

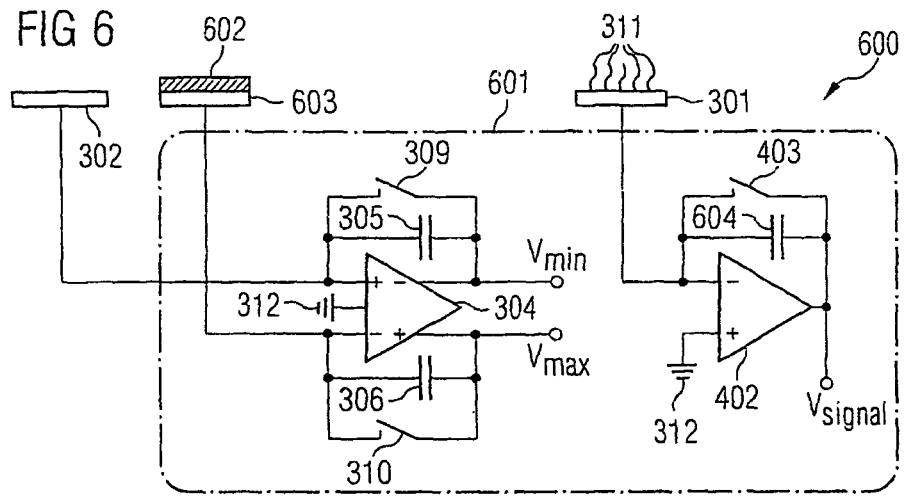
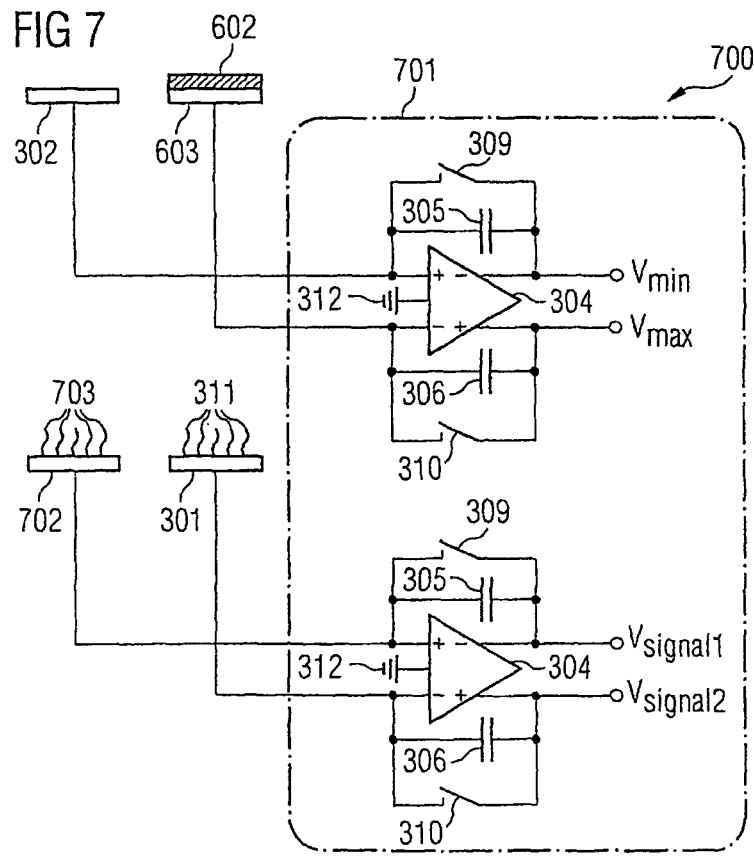

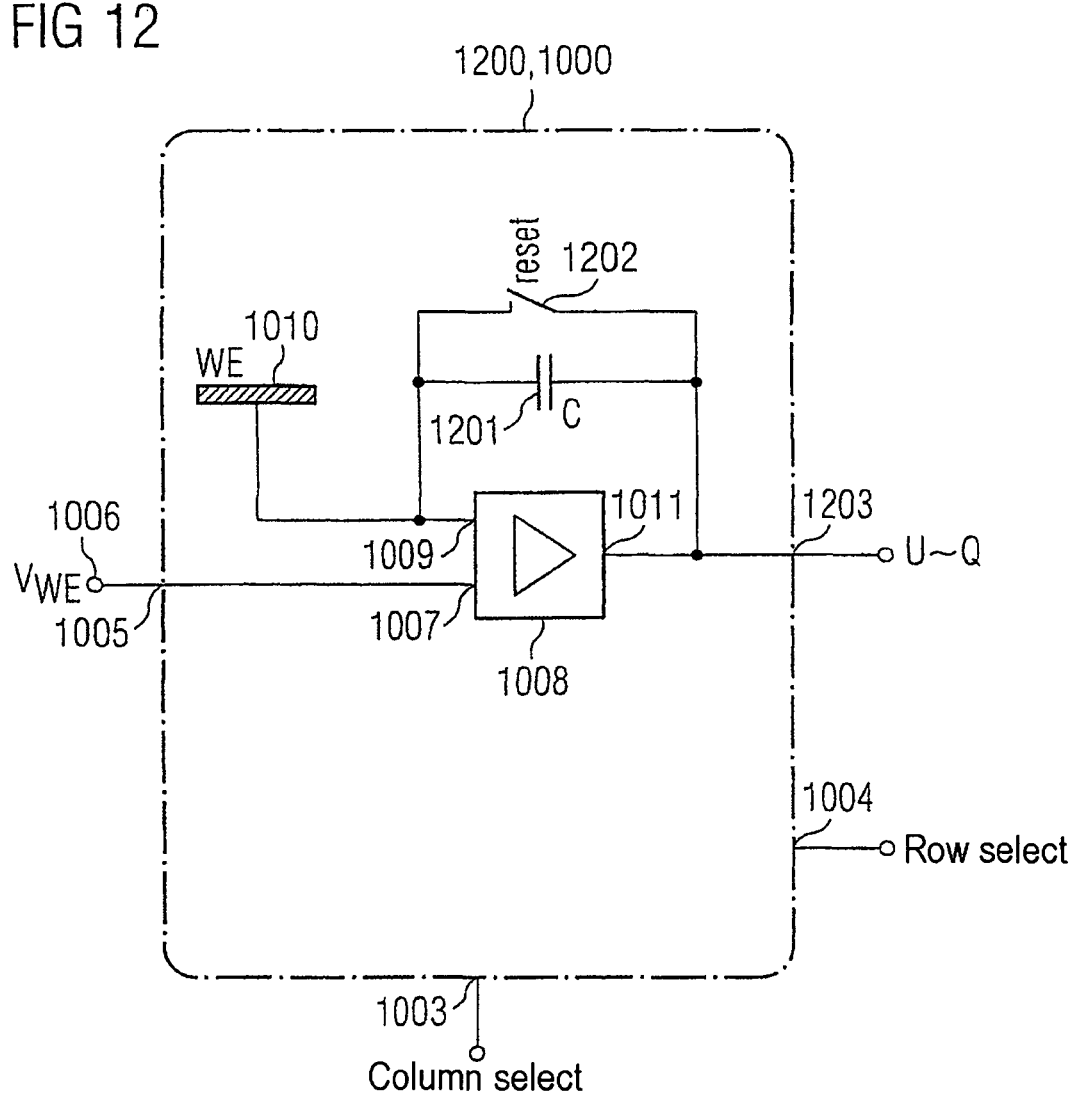

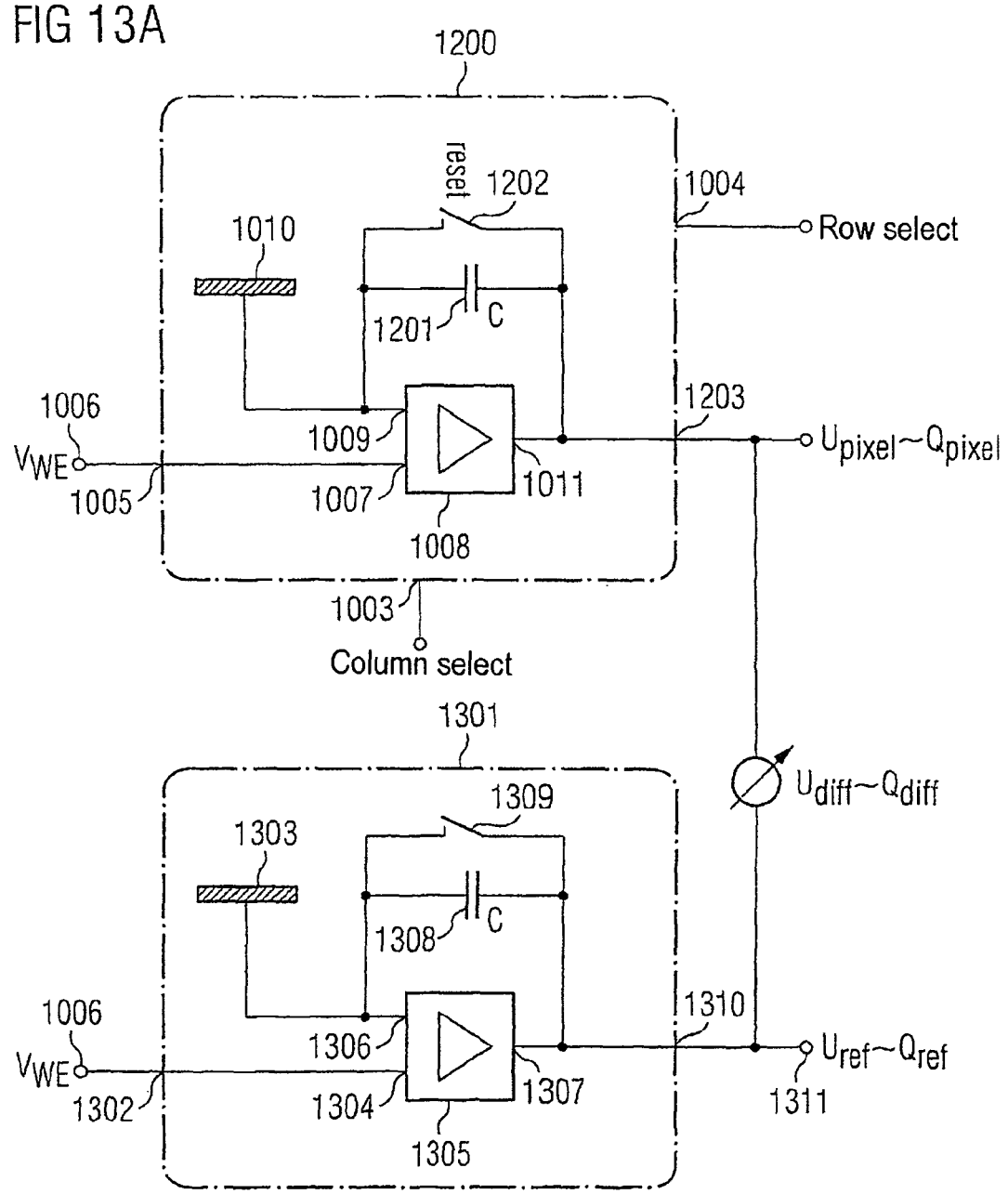

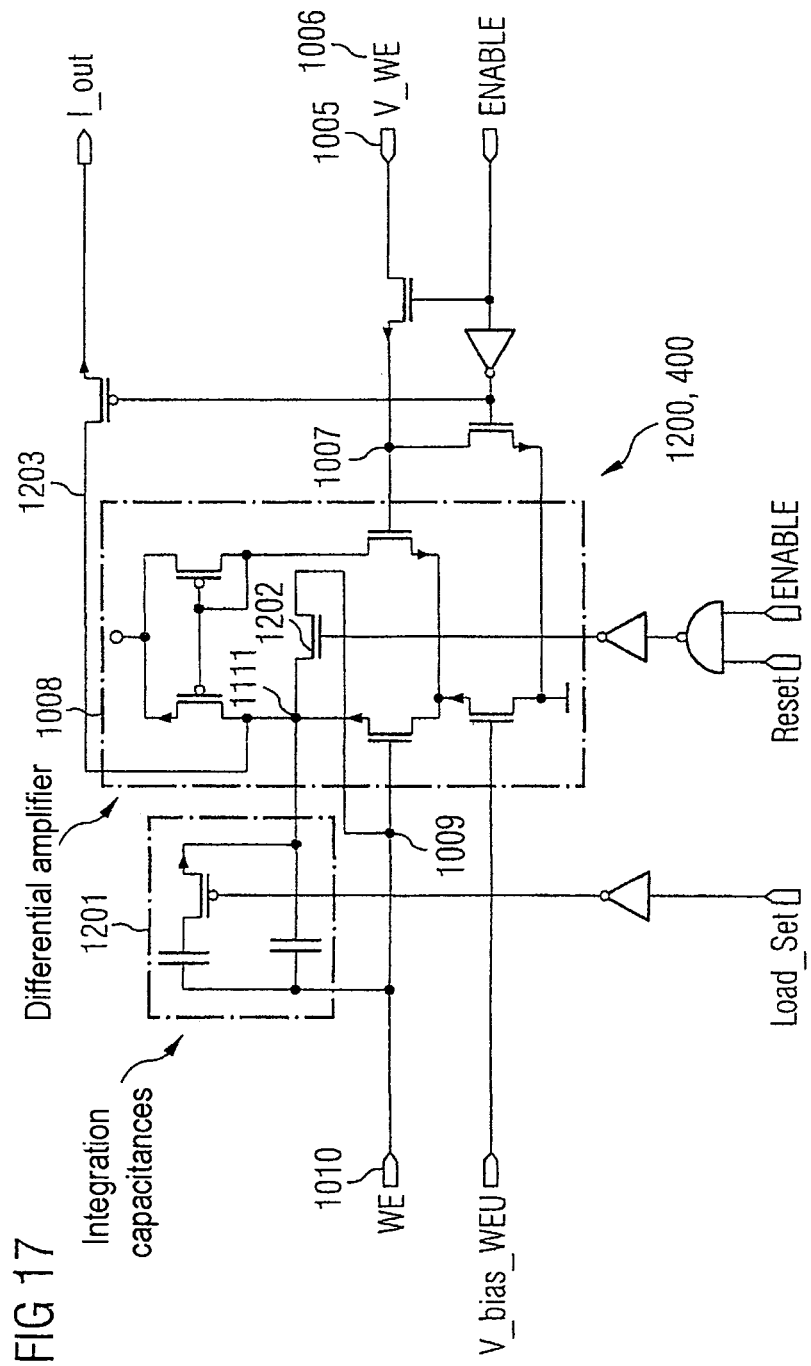

MONOLITHICALLY INTEGRATED HYBRIDISATION SENSOR ASSEMBLY AND ASSOCIATED PRODUCTION METHOD

PRIORITY STATEMENT

This application is the national phase under 35 U.S.C. §371 of PCT International Application No. PCT/DE2005/001139 which has an International filing date of Jun. 27, 2005, which designated the United States of America and which claims priority on German Patent Application number 10 2004 031 371.7 filed Jun. 29, 2004, the entire contents of which are hereby incorporated herein by reference.

FIELD

The embodiments of the invention generally relate to a monolithically integrated sensor assembly, a sensor array and/or a method for producing a monolithically integrated sensor assembly.

BACKGROUND

By way of an electrochemical analysis method, substances can be determined both qualitatively and quantitatively on account of specific physical properties using the electric current. Electrochemical analysis methods in which electrode reactions play a part are of particular importance. These are classified into two groups depending on whether the excitation signal (current, voltage or potential) is kept constant. By way of example, potentiometry, chronopotentiometry, coulometry, amperometry, dhronoamperometry and chronocoulometry are techniques in which the excitation signal is kept constant. In voltammetric and polarographic methods, the excitation signal is varied.

Together with optical methods such electrochemical analysis methods for the analytical determination of chemical and biochemical substances are characterized by a high sensitivity and also a high selectivity. Whereas, however, complicated, expensive and sensitive optical and optoelectronic apparatuses are necessary in the case of optical analysis methods, electrochemical analysis methods manage with comparatively simple electrode devices.

An advantage of electrochemical analysis methods is the direct presence of the measurement result as an electrical signal. The latter, after analog-to-digital conversion, can be processed further directly by a computer, preferably by a personal computer.

Electrochemical analysis methods are suitable for the quantitative and qualitative measurement of substance concentrations in an electrolyte solution. Every substance has an oxidation voltage and reduction voltage, respectively, that are characteristic of the substance. It is possible to distinguish between different substances on the basis of these voltages. Furthermore, the concentration of a substance present can be deduced on account of the electric current that flowed during a reaction.

An electrochemical experiment requires at least two electrodes which are connected to the substance to be analyzed in electrolytic solution (working electrode, counterelectrode). However, it is also possible to use a plurality of working electrodes in parallel. Usually a reference electrode is additionally used for exact supervision of the electrolyte potential. This system having at least three electrodes is connected to a potentiostat, which makes it possible to regulate the potential at the working electrode and measures the electric current flowing through the working electrode.

In the case of voltammetry, a variable voltage is applied to the working electrode and the current flowing during an oxidation or reduction is measured. In the special case of cyclovoltammetry, a specific voltage range is repeatedly swept over in such a way that the constituents of the electrolyte are repeatedly successively oxidized and reduced.

In the case of chronoamperometry, a defined voltage is applied discontinuously to the working electrode and the current that flows is recorded over time. This measurement method permits the analysis of a specific substance by targeted oxidation or reduction of said substance. The current that flowed is a measure of the quantity of substance converted per unit time and permits conclusions to be drawn with regard to the concentration of the substance and with regard to the diffusion constant.

Chronocoulometry corresponds to chronoamperometry in terms of the electrical boundary conditions. In contrast thereto, however, the total electrical charge that flowed is recorded rather than the electric current that flowed.

In the configuration as sensors, electrode devices can be used in various electrochemical analysis methods. All that is crucial is that substances that can be evaluated electrochemically are generated during the sensor event. In the case of sensors for the detection of biomolecules, use is made of a marking method, by way of example, which provides electrochemically active substances in the case of a sensor event.

Miniaturized electrochemical electrode systems for the analysis of chemical and biochemical substances are known in the prior art, see for example [1], [2], [3], [4] and [5]. The electrodes of such arrays can be individually contact-connected at the edge of the substrate and be operated by means of a potentiostat. In order, moreover, to realize electrode arrays which have for example 100 or more electrodes, switching functions on the substrate which multiplex the electrodes onto common connecting lines are advantageous. If the substrate is a semiconductor material, such as silicon, the required switches may be realized by MOS transistors, as described in [6]. On account of the parallelization that can thereby be achieved in the tests, the analysis time is significantly shortened and it also becomes possible to carry out complex analyses.

Reference [7] describes the so-called EDDA method (Electrically Detected Displacement Assay method), from the company Friz BIOCHEM™.

Reference [8] describes an electrode system for detecting molecules or molecular complexes. The assembly contains at least three electrodes, at least one working electrode, one counterelectrode and one reference electrode being present. The reference electrode is arranged in such a way that it is adjacent at least to partial regions of the two further electrodes. Furthermore, an electrode assembly described in [8] contains a plurality of operational amplifiers integrated into a substrate and serving for evaluating a sensor signal, which operational amplifiers supply the measurement signals to external evaluation units.

Reference [9] describes a biosensor for detecting macromolecular biopolymers. An electrode assembly having at least one unit for immobilizing macromolecular biopolymers is formed in the biosensor. In this case, the at least one unit is provided with catcher molecules. Furthermore, the at least one unit is set up in such a way that a medium which is to be examined and which contains biopolymers to be detected can be brought into contact with the immobilization unit. Biopolymers contained in the sample to be examined can be bound to the catcher molecules, whereby complexes composed of biopolymers and catcher molecules are formed. A first electrical measurement is carried out in order to detect the biopolymers with the aid of the biosensor. Afterward, the complexes are separated and a second electrical measurement is carried out. The biopolymers are detected by way of an alteration of the value of the electrical measurement that is brought about by the separation of the complexes.

Reference [10] describes a DNA sensor having an electrode assembly with an interdigital structure. In this case, the interdigital structure has additional reaction areas for attachment of thiols. During the operation of the sensor described in [10], so-called markers are applied to the areas covered by thiols.

Reference [11] describes an electrode assembly for detecting macromolecular biopolymers which has at least one unit for immobilizing biopolymers. The at least one unit for immobilizing macromolecular biopolymers is provided with catcher molecules, in which case the catcher molecules can bind macromolecular biopolymers, on the one hand, and on the other hand have a marking that can generate a detectable signal.

Reference [12] describes a circuit for the integration of an electric current (current integrator), which circuit has an operational amplifier, inter alia.

Reference [13] describes a circuit for the rectification of an AC voltage. In this case, a capacitor is charged during a positive half-cycle of the AC voltage by way of a forward-biased diode. During the negative half-cycle, the diode is turned off, and the voltage present at the capacitor remains approximately constant.

From the standpoint of miniaturization, signal integrity and also measurement sensitivity, the active microarrays known in the prior art constitute very good electrochemical analysis systems [2]. Such electrochemical sensor arrays that operate according to voltammetric, (chrono)amperometric and (chrono)coulometric methods are manufactured in accordance with CMOS technology and equipped with electrodes made of a noble metal (e.g. gold) which are accessible on the chip surface.

Active sensor arrays have been realized in DNA sensor chips, for example, in which, on the basis of redox cycling, DNA molecules are detected at surfaces electronically by the detection of electrical charge carriers generated by means of redox-active substances. Redox cycling constitutes a special case of an amperometric method (oxidation/reduction voltages constant, measurements of the electrode current).

A typical redox cycling sensor arrangement has two gold electrodes formed on a substrate. Single-stranded DNA catcher molecules immobilized via the so-called gold-sulfur coupling, for example, and having a predetermined sequence are immobilized on each electrode. The complementary single-stranded DNA target molecules, which are thus capable of hybridization, possibly present in the analysis solution have a marking. By way of the marking, given the presence of suitable additional molecules, a cycle of oxidation and reduction of constituents of the additional molecules is initiated, which, under interaction with the electrodes, leads to the formation of reduced or oxidized molecules. The cycle of oxidations and reductions leads to a circulating electric current that enables a detection of the DNA target molecules.

Both in the case of said redox cycling assembly and in the case of the electrochemical analysis methods mentioned above, a counterelectrode is always required. Whereas in the case of the redox cycling sensors, however, only a relatively small DC current has to be conducted away at the electrodes, in the case of most of the electrochemical analysis methods specified above it is necessary for a comparatively high surge current to be able to be supplied by the counterelectrode. For this reason, the area of the counterelectrode has to be significantly greater than that of the active working electrodes.

Depending on the concrete analysis method, a surface area approximately 10 times greater with respect to the sum of the surface areas of the individual working electrodes regularly has to be demanded for the counterelectrode. This is necessary because if the counterelectrode has an excessively small area, the voltage present at it during an experiment for providing the required charge carriers can assume extremely high values. If such high values are assumed, chemical conversions, e.g. of the electrode material, that proceed in uncontrolled fashion may be the consequence, which typically take place with the formation of gases.

If the surface area of the counterelectrode is large enough, it is able to stabilize the electrolyte potential for the most part by way of the double-layer capacitance. Electrochemical conversions take place only with comparatively low current densities.

Since an active silicon chip as a substrate, e.g. for a DNA sensor, is comparatively expensive, generally a highest possible packing density of the individual sensors in the array is striven for. Owing to the packing density of the sensors and thus of the electrodes, under certain circumstances it is not possible to realize a counterelectrode in the region of the sensor array. The counterelectrode may then be embodied as an external electrode which is arranged in the sample volume and electrically connected to the sensor chip. The driving of this electrode may be performed by a potentiostat. This procedure is disadvantageous, however, owing to comparatively long leads and the more complicated mechanical construction. If the associated disadvantages are to be avoided, the only solution offered by the prior art is to realize the counterelectrode in the periphery of the array, but this requires additional (expensive) chip area.

One important type of sensor, particularly in the case of all-electronic DNA sensor chips, is based on so-called redox cycling. Principles of redox cycling are described in [3], [4]. Redox cycling involves detecting macromolecular biopolymers at surfaces electronically by detection of electric currents caused by way of redox-active markings.

FIG. 1A, FIG. 1B show a redox cycling sensor assembly 100 in accordance with the prior art.

The redox cycling sensor assembly 100 has two gold working electrodes 101, 102 formed on a substrate 103. DNA catcher molecules 104 having a predetermined sequence are immobilized on each working electrode 101, 102. The immobilization is effected in accordance with the so-called gold-sulfur coupling, by way of example. Furthermore, an analyte 105 to be examined is introduced into the redox cycling sensor assembly 100. The analyte 105 may be for example an electrolytic solution comprising various DNA molecules.

If the analyte 105 contains first DNA single strands 106 having a sequence which is not complementary to the sequence of the DNA catcher molecules 104, then the first DNA single strands 106 do not hybridize with the DNA catcher molecules 104 (see FIG. 1A). This case is referred to as a "mismatch".

If, by contrast, the analyte 105 contains second DNA single strands 107 having a sequence which is complementary to the sequence of the DNA catcher molecules 104, then the second DNA single strands 107 hybridize with the DNA catcher molecules 104. This case is referred to as a "match". To put it another way, a DNA single strand 104 having a predetermined sequence is in each case only able to hybridize selectively with a very specific DNA single strand, namely with the DNA single strand having a sequence that is complementary to the respective catcher molecule.

As shown in FIG. 1B, the second DNA single strands 107 to be detected contain a redox-active marking 108. After the hybridization of the second DNA single strands 107 to be detected with the DNA catcher molecules 104, by way of the redox-active marking 108 (e.g. an enzyme label such as e.g. an alkaline phosphatase), given the presence of suitable additional molecules 109 (for example para-aminophenyl phosphate, p-APP), a cycle of oxidations and reductions of constituents of the additional molecules 109 is initiated, which, under interaction with the gold electrodes 101, 102, leads to the formation of reduced molecules 110 (e.g. para-aminophenol) and oxidized molecules 111 (e.g. quinone imine). The cycle of oxidations and reductions leads to a circulating electric current that enables a detection of the second DNA single strands 107.

Consequently, in the redox cycling method, in the case of a binding event between a particle to be detected and a catcher molecule by means of an enzyme label (e.g. an alkaline phosphatase), a redox-active species is produced by means of para-aminophenyl phosphate (p-APP), contained in an electrolyte for example being converted into para-aminophenol. Since new redox-active species are constantly generated, this leads to a rise in the electric current between the two electrodes.

An oxidizing electrical potential is required at the first working electrode 101, which may also be referred to as generator electrode. A reducing electrical potential is required at the second working electrode 102, which may also be referred to as collector electrode.

FIG. 2 shows an interdigital electrode arrangement 200 known from the prior art, which assembly has two interdigitated working electrodes, namely a generator electrode 201 and a collector electrode 202. A reference electrode 203 and a counterelectrode 204 are furthermore shown. The electrodes 201 to 204 are formed on a substrate 205. An electrolytic analyte (not shown) may be applied to the interdigital electrode arrangement 200, said analyte being coupled to the electrodes 201 to 204.

The electrical potential of the electrolytic analyte is provided, by way of the reference electrode 203, at an inverting input of a comparator 206 and compared by the latter with a desired electrical potential at the noninverting input of the comparator 206. In the case where the electrical potential of the reference electrode 203 deviates from the desired potential, the counterelectrode 204 is driven via an output of the comparator 206 in such a way that said counterelectrode subsequently supplies electrical charge carriers as required in order to maintain the desired electrical potential of the electrolyte. The reference electrode 203 together with the comparator 207 clearly forms a potentiostat device. The electrical potentials at the working electrodes 201, 202 are set relative to the reference voltage. First and second ammeters 207, 208 are used to detect electric sensor currents of the generator electrode 201 and of the collector electrode 202, respectively, which contain items of information about a sensor event that has possibly taken place.

The prior art furthermore discloses a sensor array in which a plurality of interdigital electrode assemblies 200 are connected up to one another in matrix-type fashion, for example. In said array, components 203, 204, 207, 208 may be provided jointly for a plurality of sensor zones.

Circuit architectures for biosensors are known which serve for the sensitive detection of biomolecules by way of electrochemical conversions in electrolyte solutions. In this case, in particular the hybridization of two complementary oligonucleotides is detected by means of the presence of known electrochemical markings (e.g. a Ferrocen marking). The electrical measurement of the electrochemical markings present on the surface of the sensor electrode is effected by means of an abrupt change in the electrode voltage. In this case, the markings are oxidized or reduced in a targeted manner. The value of the current that occurs in the process is a measure of the quantity of the marking present on the sensor surface. In this case, the current surge or the quantity of charge is composed of electrical charges which flow into the double-layer capacitance at the electrode surface and the charges which emerge from oxidation and reduction processes.

In accordance with the prior art, an absolute value of an electrical charge quantity that occurs during a voltage surge is measured at one sensor electrode. What is disadvantageous in this case is that large quantities of such electrical charge carriers which do not contribute to the measurement signal and thus impair the noise margin are also detected in an undesirable manner.

Reference [14] describes an all-electronic DNA sensor array chip that uses a redox cycling method, the individual sensors of the array in each case having an electrode assembly with an interdigital structure and also a potentiostat circuit. The DNA sensors has 128 sensor positions, an analog-to-digital conversion of the respective sensor signal being effected in each individual pixel. The chip is realized using a CMOS process.

SUMMARY

In at least one embodiment, a sensor assembly is provided which has an improved detection sensitivity and has an improved signal-to-noise ratio by comparison with the prior art.

In at least one embodiment, a monolithically integrated sensor assembly includes a sensor array and, in at least one embodiment, a method is disclosed for producing a monolithically integrated sensor assembly.

The monolithically integrated sensor assembly according to at least one embodiment of the invention for detecting particles possibly contained in an analyte contains a substrate, at least one sensor electrode which is arranged on and/or in the substrate and which can be coated with a sensor-active layer at which are generated electrochemically active particles (e.g. redox-active particles, electrically charged particles) in the presence of particles to be detected, which electrochemically active particles can be detected by the detection of an electrical sensor signal at the at least one sensor electrode, at least one additional electrode which is arranged on and/or in the substrate, at least one comparison electrode at which an electrical comparison signal independent of the sensor signal can be detected, and an operating circuit integrated on and/or in the substrate and serving for driving the at least one sensor electrode and the at least one additional electrode, the operating circuit having at least one evaluation unit by which a sensor event can be determined at the at least one sensor electrode on the basis of the sensor signal and the comparison signal.

Furthermore, at least one embodiment of the invention provides a sensor array including a plurality of sensor assemblies comprising the above-described features that are formed on and/or in the substrate.

In a method according to at least one embodiment of the invention for producing a monolithically integrated sensor assembly for detecting particles possibly contained in an analyte, there is formed on and/or in a substrate at least one sensor electrode which is coated with a sensor-active layer at which are generated electrochemically active particles (e.g. redox-active particles, electrically charged particles) in the presence of particles to be detected, which electrochemically active particles can be detected by the detection of an electrical sensor signal at the at least one sensor electrode. Furthermore, at least one additional electrode is formed on and/or in the substrate. At least one comparison electrode is formed, it being possible for an electrical comparison signal independent of the sensor signal to be detected at the at least one comparison electrode.

Furthermore, an operating circuit for driving the at least one sensor electrode and the at least one additional electrode is integrated on and/or in the substrate, the operating circuit having an evaluation unit by which a sensor event can be determined at the at least one sensor electrode on the basis of the sensor signal and the comparison signal.

One aspect of at least one embodiment of the invention is to be seen in the fact that a monolithically integrated sensor assembly is provided including a plurality of electrodes, having at least one sensor electrode (that is to say a working electrode), an operating circuit coupled to the working electrode and serving for driving the working electrode and also at least one additional electrode. The at least one additional electrode has one or more comparison electrodes for carrying out a comparison measurement/calibration measurement, it being possible for a measurement at the sensor electrode to be evaluated jointly with the comparison measurement by way of the integrated operating circuit. The at least one additional electrode may also have a counterelectrode, at least one reference electrode and also a potentiostat circuit for providing a predetermined potential.

The monolithically integrated sensor assembly is provided with at least one comparison electrode at which an electrical comparison signal can be detected, and the operating circuit has at least one evaluation unit by which a sensor event can be determined at the at least one sensor electrode on the basis of the sensor signal and the comparison signal.

A comparison electrode is understood to mean an electrode at which in a manner similar to that at a sensor electrode, a signal can be detected (e.g. a background, noise or zero signal independent of sensor events), which can be evaluated jointly with a sensor signal of the sensor electrode (e.g. a signal which is dependent on sensor events and which may contain a background, noise or zero signal as additional component) (e.g. difference formation in order to eliminate a background, noise or zero signal).

By contrast, a reference electrode is understood to mean, in particular, an electrode by means of which an analyte potential can be measured, and which can therefore be embedded in particular into the functionality of a potentiostat circuit in order to keep the analyte potential constant.

In contrast to the prior art, according to which the operating circuit or the potentiostat circuit is arranged externally to the electrode assembly and is connected to the latter via cables, the operating circuit or the potentiostat circuit is monolithically integrated into the sensor assembly in accordance with this aspect of at least one embodiment of the invention.

In this way, the disturbances (caused by the so-called antenna effect) of the relatively small electric currents that occur in the sensor and are to be detected, the disturbances occurring on account of the relatively long electrical leads (cables) present in accordance with the prior art, are considerably reduced according to at least one embodiment of the invention. Thus, the processable signal bandwidth and the resolution that can be achieved by way of the sensor assembly in accordance with this aspect of at least one embodiment of the invention are considerably increased. Furthermore, an increased number of electrode systems (that is to say in each case at least one counterelectrode, at least one reference electrode and also at least one working electrode) can be operated simultaneously in accordance with this aspect of at least one embodiment of the invention.

Furthermore, the monolithically integrated sensor assembly may have one or more digital control device(s) and/or analog control device(s) for controlling the electrode system(s), and also preferably peripheral circuits, which are likewise all integrated into the sensor assembly.

Furthermore, the measurement electronics for the detection and processing of the electrical signals from the operating circuits of the working electrodes are preferably likewise integrated into the monolithically integrated sensor assembly.

In accordance with one configuration of this aspect of at least one embodiment of the invention, the potentiostat circuit is set up and coupled to the counterelectrode in such a way that the predetermined potential is provided as a constant potential of the electrolyte (constant electrolyte potential). The voltage change required in the context of sensor operation is generated by the operating circuit and fed to the working electrode.

In the case of this electrochemical method in which the electrolyte potential is kept essentially constant, relative to the supply voltage of the electronic chip, the potentiostat circuit always operates at the same operating point, that is to say that it compares the electrolyte voltage provided to it by the reference electrode with a fixedly predetermined reference voltage and drives the counterelectrode in such a way that the electrolyte potential remains essentially constant. The voltage change at the working electrode that is necessary in all the electrochemical experiments mentioned is in this case ensured by the operating circuit coupled to the working electrode. The operating circuit or, if appropriate, the plurality of operating circuits obtain a temporally variable voltage for the working electrodes and regulate the electric current flow from and to the working electrode or working electrodes in such a way that the electrical voltage at the working electrode or the working electrodes follows said voltage.

The electric current that flows represents the measurement signal used for the evaluation of the electrochemical conversions at the working electrode or at the working electrodes. The potentiostat circuit operates autonomously and stabilizes the bath potential, that is to say the electrical potential in the electrolyte, at the reference potential. This procedure is advantageous particularly when different electrical potentials have to be applied to a plurality of different working electrodes accommodated in a common reaction volume.

In the context of voltammetry, a continuously changing electrical voltage is applied to the working electrode and the electric current that flows is measured. If the electrical voltage is repeatedly altered between two limit values, then this is referred to as cyclovoltammetry. The electric current that flows at the working electrode or the working electrodes is detected by suitable measurement electronics and processed further.

In the context of chronoamperometry, the electrical potential at the working electrode is discontinuously put at a specific predetermined value and the electrode current that varies temporally on account of the oxidation processes and/or reduction processes taking place is measured.

In the context of chronocoulometry, instead of the electrode current, the electrical charge that flowed is measured at the working electrode. This may be done by integration of the electrode current in an analog integrator circuit, that is to say via a capacitor, or by digitization of the electrode current and subsequent digital integration.

In accordance with another configuration of this aspect of at least one embodiment of the invention, the potentiostat circuit is set up and coupled to the counterelectrode in such a way that the electrical potential presently prevailing in the electrolyte is fed to a first input of the potentiostat circuit, and that the voltage change required for sensor operation is fed as a temporally variable electrical voltage to a second input of the potentiostat circuit and the electrical potential present at the counterelectrode is thus configured in temporally variable fashion. The operating circuit generates an electrical potential and feeds the latter to the working electrode in such a way that the electrical potential present at the working electrode is kept essentially constant temporally.

In this electrochemical method in which the electrical potential at the working electrode is kept essentially constant, relative to the supply voltages of the electronic chip into which the monolithically integrated sensor assembly is integrated, the electrical potential at the working electrodes is kept constant and the electrical potential of the electrolyte is varied.

This is of particular interest for the case where all the working electrodes in a reaction volume have to have the same effective oxidation voltage or reduction voltage. Consequently, this configuration is suitable in particular in the case of relatively large sensor assemblies having a large number of sensor zones in which each individual sensor detects the concentration of a specific electrochemically active substance that is identical for all the sensors, that is to say that this configuration is suitable in particular for electrical DNA sensors.

Clearly, in accordance with this configuration, the desired temporally variable bath voltage, that is to say the voltage of the electrolyte, is applied to one input of the potentiostat circuit, and is compared with the electrical potential of the reference electrode. The desired temporally variable bath voltage is set by way of the potentiostat circuit via the counterelectrode. The working electrode circuits, that is to say the operating circuits, keep the working electrodes or the working electrode at an essentially constant electrical potential and measure the current necessary for this purpose or the necessary quantity of charge.

The separation of the device for the voltage change (that is to say the potentiostat circuit) and the device for current measurement or charge measurement (that is to say the operating circuit) considerably simplifies the circuit design.

In particular for experiments in which a voltage jump is carried out, the architecture described above has considerable advantages with regard to the temporal behavior, the stability and also the measurement accuracy of the sensor assembly.

In the context of voltammetry, a continuously changing voltage is applied to the potentiostat, that is to say to the potentiostat circuit. The electrolyte follows this voltage change on account of the corresponding driving of the counterelectrode via the potentiostat circuit, and the electric current that flows at the working electrodes is measured. If the electrical voltage is repeatedly altered between two limit values, then this procedure is referred to as cyclovoltammetry. The electric current that flows at the working electrode is detected by suitable measurement electronics, if appropriate likewise integrated into the sensor arrangement, and processed further.

In the context of chronoamperometry, the potential of the potentiostat circuit is discontinuously put at a predetermined specific value and the electric current at the working electrode that varies temporally on account of the oxidation processes and/or reduction processes taking place is measured.

In the context of chronocoulometry, instead of the electrode current, the electrical charge that has flowed is measured at the working electrode. This may be done, on the one hand, by integration of the electrode current at an analog integrator circuit (that is to say by way of a capacitor) or by digitization of the electrode current and subsequent digital integration.

Particularly when the electrodes have very small surfaces, it is advantageous to keep the working electrodes at a constant electrical potential with respect to the operating voltage of the electronic chip and to change the voltage of the electrolyte. In this case, the parasitic input capacitance of the operating circuit for the working electrodes remains at a constant electrical potential and is not subjected to charge reversal in the case of a voltage change. The parasitic input capacitance, which, in the case of small electrodes, is of the same order of magnitude as the double-layer capacitance of the electrode itself, does not lead to a corruption of the measurement result in this case.

One aspect of at least one embodiment of the invention can clearly be seen in the fact that provision is made of a monolithically integrated electrochemical analysis system for a highly sensitive and extremely parallel detection of electrochemically active species by means of voltammetry, chronoamperometry and/or chronocoulometry.

In particular the above-described method of potentiostat operation in which the working electrode potential is kept constant and the electrical potential of the electrolyte is varied instead has considerable advantages in the cases described above.

Furthermore, the sensor assembly according to at least one embodiment of the invention is highly advantageous for so-called voltage jump experiments on account of the suitable circuitry measures with the electrical circuits monolithically integrated into the sensor assembly, in order to ensure the stability of the sensor assembly during the voltage jump experiment.

The monolithic integration of electrodes and operating circuit makes it possible to realize highly dense and highly sensitive sensor arrays whilst complying with the high edge steepness required for the voltage jump experiments.

In the case of the monolithically integrated sensor assembly of at least one embodiment of the invention, the at least one additional electrode may have at least one counterelectrode and at least one reference electrode, and a potentiostat circuit serving for providing a predetermined potential may be integrated on and/or in the substrate.

The substrate is preferably a wafer, for example a silicon wafer, in particular a silicon chip, which may be embodied as a CMOS chip. In accordance with this configuration, the sensor assembly is monolithically integrated in the CMOS chip as substrate.

In particular, the operating circuit—having an evaluation functionality—of the sensor assembly according to the invention may be monolithically integrated in the substrate, so that signals can be evaluated on-chip, whereby the signal paths are kept short and, particularly in the case of small signal amplitudes, the signal is exposed to an undesirable attenuation, damping or interference only on a short transport path. The detection sensitivity is increased as a result.

In accordance with one important aspect of at least one embodiment of the invention, a sensor assembly does not merely encompass the detection of a single absolute value of an electrical sensor signal at a sensor electrode, rather an electrical comparison signal, which is generated independently of a sensor event, is additionally detected at a comparison electrode. Consequently, the comparison signal includes those effects which are independent of the sensor event, and which may also be contained in the detected sensor signal and thus reduce the accuracy of the measurement. By virtue of the evaluation unit of the sensor assembly according to the invention jointly evaluating the sensor signal and the comparison signal, contributions to the sensor signal which do not originate from the sensor event can be eliminated, whereby the detection sensitivity is increased, the signal-to-noise ratio is improved, and the noise margin is thus increased.

The comparison signal independent of the sensor event can be subtracted from the sensor signal, it being possible to eliminate in particular signal components which are based on electrical charges which flow into a double-layer capacitance of an electrode surface. Consequently, at least one embodiment of the invention provides a particularly advantageous circuit architecture which enables an advantageous operation in particular of electrical biosensors, more particularly the operation of electrochemical biosensors according to the measurement principle of coulometry.

Clearly, the configuration described provides a circuit arrangement which uses at least two electrodes, namely at least one sensor electrode and at least one comparison electrode, for the detection of a measurement signal. One of the electrodes is set up and operated as a measuring electrode or sensor electrode, that is to say that this electrode bears a sensor-active layer, which may be a biosensitive or chemosensitive coating. In a region surrounding said measuring electrode, an additional electrode, which is also referred to as comparison or difference electrode, is provided, which is likewise in electrical contact with an analyte to be examined, but can supply no or an exactly defined measurement signal on account of its lack of coating or different coating with respect to the measuring electrode.

During a measurement, the comparison electrode carries out the same voltage jump as a measuring electrode. In the case of a comparison electrode, the same disturbing charges as in a measuring electrode will then occur (for example brought about by the charge reversal of the double-layer capacitance, undesirable oxidations/reductions of unknown substances in an analyte, etc.). The comparison electrode may have exactly the same geometry as the sensor electrode, so that approximately the same disturbing charge as at the sensor electrodes occurs there.

By way of the circuit technology according to at least one embodiment of the invention, formation of a difference between the measurement signal of the sensor electrode and the comparison signal of the comparative electrode can already be carried out in the sensor pixel, that is to say on-chip. The resulting signal, preferably a difference signal formed from the two detected signals mentioned, is then a measure of the pure measurement signal, which is free of undesirable disturbing contributions, and represents exclusively the charge carriers that emerged from desired oxidations or reductions at the sensor-active layer.

Consequently, the sensor assembly according to at least one embodiment of the invention significantly improves the noise margin and increases the resolution of the measuring system.

As an alternative to one comparison electrode per sensor assembly, in a sensor array comprising many sensors of identical type, at least one comparison electrode may be provided jointly for the entire array. The signal of the comparison measurement may be provided for example to all the sensor pixels for difference formation. If said signal is obtained from a plurality of comparison electrodes, a statistical averaging of the comparison signals of the plurality of comparison electrodes leads to a very exact reference value to which the measured values can be referred.

The comparison electrode preferably has the same geometry as the measuring electrodes, thereby preventing area effects and edge effects from influencing the signal of the two electrodes in different ways. If the geometries are different, the two signals have to be coordinated with one another. Since the quantities of charge rise to a first approximation linearly with the surface area of the electrode, it is possible to take account of the area ratio by way of a corresponding scaling of the signals during the difference formation.

The at least one comparison electrode is preferably free of signaling substances. That is to say that the sensor event of a measuring electrode (e.g. complexing, hybridization, etc.) only brings about a negligible change in the electrochemical properties of a comparison electrode. In the case of a voltage jump characteristic of coulometry, therefore, charge carriers from the charge reversal of the electrochemical double layer exclusively occur in that case, as well as parasitic oxidations or reductions. The signaling substances are exclusively implemented at the at least one sensor electrode (measuring electrode).

As an alternative, a comparison electrode may also be provided with a defined signaling coating, so that a known quantity of charge becomes free there in the case of a voltage jump, which quantity of charge can then be compared with the measurement signal. In this case, the signaling coating of the comparison electrode should not be influenced by a sensor event. Clearly, a "full" sensor signal can be simulated at a comparison electrode having such a defined signaling coating. That is to say that the signal at the comparison electrode is then for example just like that at a sensor electrode at which hybridization events have taken place at (almost) all the catcher molecules.

Another advantage of the difference measurement is to be seen in the fact that the electrode voltages do not have to be controlled very exactly, as would be the case for example with a single electrode system. In the case of a single electrode system, an incorrect output voltage and an incorrect target voltage lead to undesirable oxidations or reductions of substances present in an electrolyte, which contribute to the measurement signal and cannot be distinguished from the actual measurement signal of the sensor event. In the case of a difference measurement, these uncontrolled oxidations and reductions also occur at the comparison electrode and are finally subtracted from the measurement signal by way of difference formation.

If the jump voltages no longer have to be controlled very exactly, it is possible to reduce the outlay for a reference electrode that measures the electrolyte potential. In this case, a quasi reference electrode, comprising for example a noble metal electrode, which is in contact with the electrolyte, can also supply a sufficiently constant electrical potential.

One important aspect of at least one embodiment of the invention is therefore to be seen in the fact that already within a sensor pixel a measurement signal is related to one or more comparison signals (reference signals), in particular a difference measurement or difference formation is provided, whereby the noise margin is increased and the accuracy and resolution of the sensor system are thus improved.

The sensor assembly may be set up as a biosensor assembly or as a chemosensor assembly. In the case of a configuration as a biosensor assembly, the sensor-active layer may be a layer made of catcher molecules (e.g. DNA single strands) which can hybridize with particles to be detected, namely with DNA single strands complementary to the DNA catcher molecules.

In the case of a configuration of the sensor assembly as a chemosensor assembly, the sensor assembly can for example measure a gas concentration of an environment by virtue of gas atoms together with the material of the sensor-active layer generating electrochemically active constituents, e.g. electrical charge carriers, which are detectable.

In the case of a configuration of the sensor assembly as a biosensor assembly, the sensor assembly may be set up for example as a DNA sensor assembly, as a protein sensor assembly or as an antibody sensor assembly.

The evaluation unit of the sensor assembly may be set up in such a way that it forms the difference between the sensor signal and the comparison signal. By means of subtracting the comparison signal from the sensor signal, signal components which are not based on a sensor event can be eliminated, whereby disturbing contributions to the measurement signal are removed.

In the case of the sensor assembly, the evaluation unit may have an operational amplifier which is integrated in the substrate and which processes the sensor signal and the comparison signal.

In the case of the sensor assembly, the operational amplifier may be set up for the integration of electrical charge carriers. The provision of a monolithically integrated comparator and/or of a monolithically integrated operational amplifier enables a space-saving, effective and simple on-chip processing of the signals and thus ensures a high signal-to-noise ratio.

The at least one comparison electrode of the sensor assembly may be free of a sensor-active layer. In such a case, it is ensured that sensor events in a region surrounding the comparison electrode do not lead to a signal. Consequently, signal components of the comparison signal are only governed by background components, which can thus be subtracted from the signal of the sensor electrode in order to eliminate background components from the signal of the sensor electrode.

In the case of the sensor assembly, the at least one comparison electrode may have a signaling coating that generates a predeterminable quantity of electrochemically active particles in the case of a predeterminable change in the electrical potential, independently of the sensor event. In accordance with this configuration, the signaling coating is set up in such a way that it does not generate a signal in the case of a sensor event. The signal generated by the signaling coating may be a defined signaling coating which, by way of example, releases a known quantity of charge in the case of a voltage jump, which quantity of charge can then be compared with a measurement signal. However, said signaling coating of the comparison electrode should not be influenced by a sensor event.

The at least one sensor electrode and the at least one comparison electrode may have an essentially identical geometry. In other words, the sensor electrode and the comparison electrode may be formed in a very similar manner, in particular have the same active surface, or at least have surfaces which are in a predetermined definable ratio with respect to one another. The signals, namely the sensor signal and the comparison signal, can then be compared particularly well with one another.

In the case of the sensor assembly, provision may be made of a plurality of comparison electrodes, it being possible to determine a sensor event at at least one sensor electrode on the basis of the sensor signal and the comparison signal of the plurality of comparison electrodes. By carrying out a statistical averaging of a plurality of comparison signals from a plurality of comparison electrodes, the comparison signal is particularly reliable and independent of statistical fluctuations if it is subtracted from the sensor signal.

The sensor assembly may include a device for keeping constant the electrical potentials at the at least one sensor electrode and at the at least one comparison electrode. Such a device for keeping constant the electrical potentials may be realized by way of at least one capacitance, preferably by way of a first capacitance for the sensor electrode and a second capacitance for the comparison electrode. By coupling one terminal of the two capacitances to the respectively associated electrode, it is possible to couple the other terminal to an output of an operational amplifier at whose input the signals of the respective electrodes are provided. An assembly of this type integrates the charge carriers occurring during a voltage jump at the sensor electrode and comparison electrode.

Furthermore, provision may be made of a subtraction capacitance for forming the difference between the sensor signal and the comparison signal, it being possible for a first terminal of the subtraction capacitance to be coupled to the at least one sensor electrode, and it being possible for a second terminal of the subtraction capacitance to be coupled to the at least one comparison electrode. These measures enable the electrical charges linked with the sensor signal and with the comparison signal to be subtracted directly from one another by conducting them to terminals of the subtraction capacitance.

Furthermore, a first comparison electrode may be provided, at which a zero signal can be generated. Moreover, a second comparison electrode may be provided, at which a full signal can be generated. The zero signal is a signal which contains only background components and which is independent of a sensor event. The full signal corresponds to a maximal signal. A sensor signal at the sensor electrode can then be related to the zero signal and to the full signal, and generally lies between the zero signal and the full signal, as a result of which quantitative statements can be made about a sensor event.

The sensor assembly according to at least one embodiment of the invention may have an analog/digital converter for forming a digital output signal on the basis of the sensor signal and the comparison signal. Such a digital signal can be transported in a manner free of interference, whereby the detection sensitivity is again increased. This holds true particularly when the analog/digital converter is realized on-chip.

The zero signal and the full signal may form the upper and the lower electrical reference potential of the analog/digital converter. In the case of an analog/digital converter, a reference voltage, formed from the difference between full signal and zero signal, is progressively reduced at a cascade of gradation elements, and compared with a sensor signal. A thermometer code, that is to say a digital signal that is a measure of the sensor events that have taken place, is provided at the output of comparators of such an analog/digital converter.

The sensor array according to at least one embodiment of the invention, which has sensor assemblies according to the invention, is described in more detail below. Configurations of the sensor assemblies also hold true for the sensor array, and vice versa.

The sensor array may have a drive unit set up in such a way that it can be used to selectively drive one sensor assembly, a portion of the sensor assemblies or all of the sensor assemblies.

Consequently, either all the sensor assemblies of the sensor array can be operated simultaneously and also be driven or read simultaneously, or individual sensor assemblies from among the sensor assemblies can be progressively selected successively. Row-by-row or column-by-column selection of sensor assemblies in a matrix-type assembly of sensor assemblies is also possible.

In the case of a sensor array, it is furthermore possible for at least one of the comparison electrodes to be provided jointly for at least one portion of the sensor assemblies. It is thus possible, for miniaturization of the sensor array, to provide fewer comparison electrodes than sensor assemblies, so that a plurality of sensor assemblies then share one and the same comparison electrode.

BRIEF DESCRIPTION OF THE DRAWINGS

Example embodiments of the invention are illustrated in the figures and are explained in more detail below.

In the figures:

FIGS. 1A, 1B show different operating states of a redox cycling sensor assembly in accordance with the prior art, FIG. 4 shows a sensor assembly in accordance with a second example embodiment of the invention, FIG. 5 shows a sensor assembly in accordance with a third example embodiment of the invention, FIG. 6 shows a sensor assembly in accordance with a fourth example embodiment of the invention, FIG. 7 shows a sensor assembly in accordance with a fifth example embodiment of the invention, FIG. 12 shows the pixel circuit in accordance with FIG. 10 in a simplified illustration, FIGS. 13A and 13B show pixel circuits with reference circuits in accordance with different aspects of example embodiments of the invention, FIG. 17 shows a circuitry realization of the pixel circuit in accordance with FIG. 12.

Identical or similar components in different figures are provided with identical reference numerals.

The illustrations in the figures are schematic and not to scale.

DETAILED DESCRIPTION OF THE EXAMPLE EMBODIMENTS

A description is given below, referring to FIG. 3, of a sensor assembly 300 in accordance with a first example embodiment of the invention.

Figure 2:
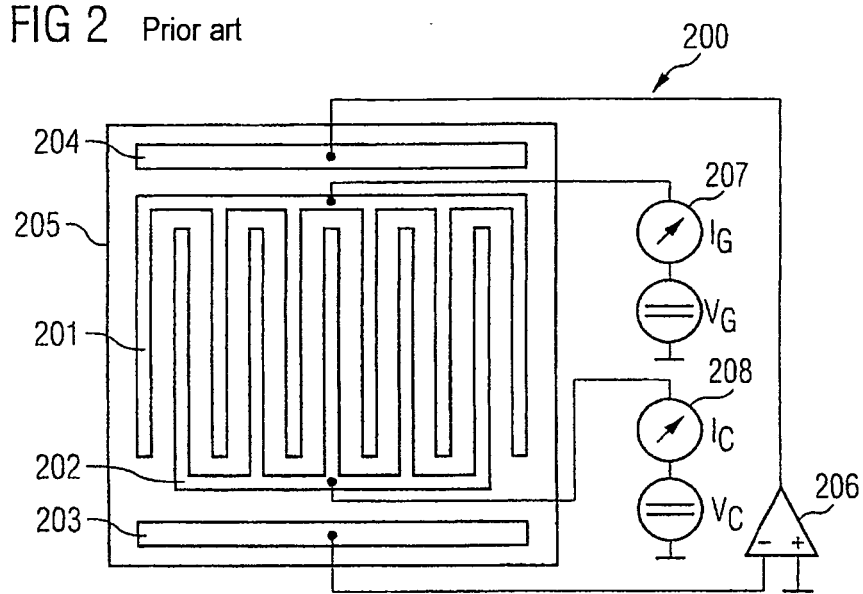
FIG. 2 shows an interdigital electrode assembly in accordance with the prior art.
Figure 3:
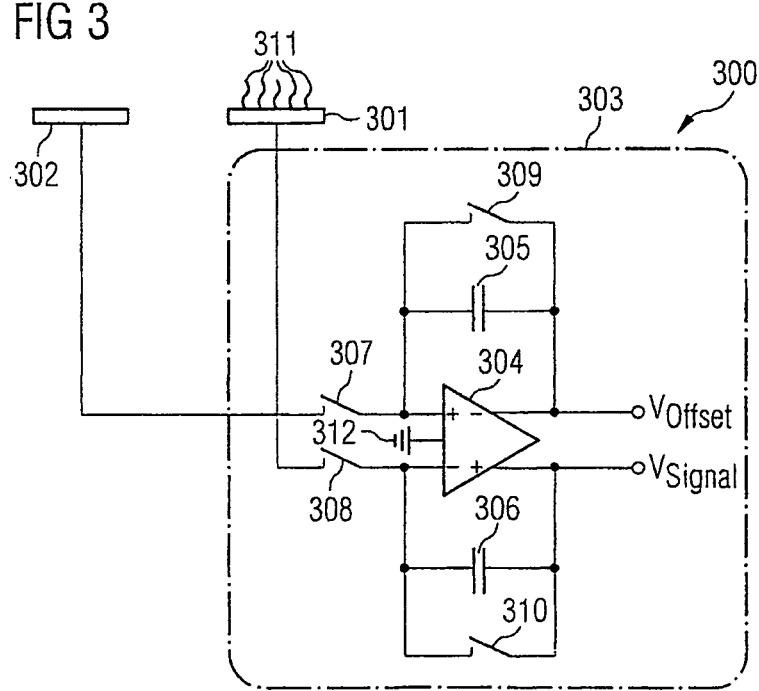
FIG. 3 shows a sensor assembly in accordance with a first example embodiment of the invention.

The sensor assembly 300 shown in FIG. 3 is set up for carrying out a sensor method of a first example embodiment. The sensor assembly 300 is set up for the detection of DNA single strands (not shown) possibly contained in an analyte (not shown) and is monolithically integrated in a silicon substrate. The sensor assembly 300 contains a sensor electrode 301 arranged on the silicon substrate and coated with DNA single strands 311 as catcher molecules, that is to say with a sensor-active layer. In the presence of DNA single strands to be detected as particles to be detected, electrochemically active particles are provided, which are detected by means of the detection of an electrical sensor signal at the sensor electrode 301.

Furthermore, a comparison electrode 302 arranged on the silicon substrate is formed in the case of the sensor assembly 300, it being possible for an electrical comparison signal to be detected at the comparison electrode. Since the comparison electrode 302 is free of catcher molecules (or is equipped with catcher molecules not ready for binding, no sensor event occurring at catcher molecules not ready for binding even in the presence of particles to be detected), the signal detected at the electrode is essentially independent of a sensor event.

Furthermore, an evaluation circuit 303 (operating circuit) is provided which is monolithically integrated in the silicon substrate and by which a sensor event is determined at the sensor electrode 301 on the basis of the sensor signal and the comparison signal. The sensor assembly 300 set up as a biosensor assembly constitutes an example embodiment of the invention in which the comparison electrode 302 is free of a sensor-active layer. In other words, no DNA single strands 311 are immobilized on the sensor electrode 302.

The sensor electrode 301 and the comparison electrode 302 have an essentially identical geometry, so that the electrical signals generated at them can be compared well with one another.

The comparison electrode 302 is coupled to a first switching element 307. The sensor electrode 301 is coupled to a second switching element 308. When the first switching element 307 is closed, the comparison electrode 302 is coupled to a positive input of a fully differential operational amplifier 304 monolithically integrated in the silicon substrate. In the closed state of the second switching element 308, the sensor electrode 301 is coupled to a negative input of the operational amplifier 304.

Furthermore, in a closed state of the first switching element 307, the comparison electrode 302 is coupled to a first terminal of a first capacitance 305 and to a third switching element 309. In the closed state of the second switching element 308, the sensor electrode 301 is coupled to a first terminal of a second capacitance 306 and to a fourth switching element 310.

An electrical comparison signal $V_{offset}$ is provided at a negative output of the operational amplifier 304, the signal being present at the second terminal of the first capacitance 305 and at a second terminal of the switching element 309. The sensor signal $V_{sensor}$ is provided at a positive output of the operational amplifier 304, the signal furthermore being present at a second terminal of the second capacitance 306 and at a second terminal of the fourth switching element 310.

A fully differential embodiment of a charge sensor is realized in the case of the sensor assembly 300. The comparison electrode 302 and the sensor electrode 301 (measuring electrode) are connected to the inputs of the fully differential operational amplifier 304. Via the integration capacitances 305, 306, precisely the quantity of charge is fed back to the electrodes 301, 302 that the electrical voltage of the two electrodes 301, 302 always remains constant. The operational amplifier 304 is equipped with a common-mode connection which ensures that the electrical potential at the inputs has a predeterminable value (represented by the electrical ground potential at the ground terminal 312 in FIG. 3). Operation with a constant electrode voltage is provided if the electrochemical voltage jump is affected by the electrolyte potential. If the electrolyte potential is intended to remain constant, by contrast, the electrode voltage can also be altered discontinuously by way of the common-mode voltage at the operational amplifier 304.

Two voltage signals $V_{offset}$ and $V_{signal}$ each proportional to the detected quantity of charge at the sensor electrode 301 and at the comparison electrode 302, respectively, are obtained at the output of the evaluation circuit 303. If a voltage is measured between these two terminals, that is to say $V_{signal}$-$V_{offset}$, then the difference signal free of those signal components of $V_{signal}$ which are not based on a sensor event and are therefore also contained in $V_{offset}$ is obtained directly. The values of the first and second capacitances 305, 306 define the sensitivity of the sensor assembly 300 to the comparison signal and measurement signal, respectively. Both electrodes 302, 301 preferably have the same geometry, so that identical integration capacitors 305, 306 are expediently used.

The third and fourth switching elements 309, 310, clearly reset switches, serve for initializing the circuit, that is to say for erasing charges from previous measurements.

The first and second switching elements 307, 308, clearly storage switches, between the electrodes 301, 302 and the input lines at the inputs of the operational amplifier 304 serve for storing the measurement signal in the integration capacitances 305 and 306, respectively, after measurement has been effected. There can then be a comparatively long time between the end of the measurements and the read-out of the result, which is advantageous particularly in the case of large sensor arrays including a large number of sensor assemblies 300.

The switches 307 to 310 are not illustrated in the example embodiments described below, but can, of course, also be provided in each case therein.

A description is given below, referring to FIG. 4, of a sensor assembly 400 in accordance with a second example embodiment of the invention.

The sensor electrode 301 is coupled to the inverting input of a first comparator 401, the noninverting input of which is coupled to the ground terminal 312. An output of the first comparator 401 is connected to a first output terminal of the evaluation circuit 406, at which the signal $V_{difference}$ is present. Furthermore, the output of the first comparator 401 is fed back to the inverting input of the first comparator 401 via a seventh switching element 405.

Moreover, the output of the first comparator 401 is fed back to the inverting input of the comparator 401 via the second capacitance 306. The sensor electrode 301 is furthermore coupled to a first terminal of a sixth switching element 404 and to a first terminal of a third capacitance 305, the second terminals of the sixth switching element 404 and of the third capacitance 407 being coupled to one another and to a first terminal of a fifth switching element 403. The first terminal of the fifth switching element 403 is furthermore coupled to a second output terminal of the evaluation circuit 406 (operating circuit), at which the signal $V_{offset}$ is provided.

Furthermore, the second terminal of the fifth switching element 403 is coupled to a first terminal of the first capacitance 305, to the comparison electrode 302 and to an inverting input of a second comparator 402. A noninverting input of the second comparator 402 is coupled to the ground terminal 312. The output of the second comparator 402 is coupled to a second terminal of the first capacitor 305 and to the first terminal of the fifth switching element 403.

In the case of the sensor assembly 400 shown in FIG. 4, the difference signal $V_{difference}$ between the signals at the measuring electrode 301 and at the comparison electrode 302 is already output as the output signal. This is achieved by way of the preferably same quantity of charge which is conducted by the sensor arrangement 400 via the first capacitance 305 to the comparison electrode 302 being conducted via the third capacitance 407 to the sensor electrode 301. By this, as it were a basic charge obtained at the measuring electrode 301 is provided, and the circuit section which operates the measuring electrode 301 only has to provide the remaining difference charge. Consequently, a voltage which directly represents the difference signal between the potentials at the two electrodes 301, 302 is obtained as the output signal.

A description is given below, referring to FIG. 5, of a sensor arrangement 500 in accordance with a third example embodiment of the invention.

With regard to its functionality, the sensor assembly 500 is very similar to the sensor assembly 400, even though the individual components in the evaluation circuit 501 are connected up somewhat differently than in accordance with FIG. 4.

In particular, an operational amplifier 502 is provided in the evaluation circuit 501. The comparison electrode 302 is coupled to a positive input of the operational amplifier 502. The sensor electrode 301 is coupled to a negative input of the operational amplifier 502. Furthermore, the offset signal $V_{offset}$ is provided at a negative output of the operational amplifier 502, whereas the difference signal $V_{difference}$ formed from the sensor signal at the sensor electrode 301 and the offset signal of the comparison electrode 302 is provided at a positive output of the operational amplifier 502.

A description is given below, referring to FIG. 6, of a sensor arrangement 600 in accordance with a fourth example embodiment of the invention.

In the case of the sensor assembly 600, an additional comparison electrode 603 is provided in addition to the comparison electrode 302, a signaling layer 602 being arranged on said additional comparison electrode. The signaling layer 602 can generate a maximal signal, that is to say a signal corresponding to a maximal sensor event, at the additional comparison electrode 603.

As shown in FIG. 6, the evaluation unit 601 of the sensor assembly 600 is divided into two partial units, one of which is set up for the processing of the comparison signals of the comparison electrode 302 and of the additional comparison electrode 603. With regard to its interconnection, this partial arrangement essentially corresponds to the interconnection shown in FIG. 3. The first (lower) comparison signal $V_{min}$ is provided at the negative output of the operational amplifier 304, whereas the second (upper) comparison signal $V_{max}$ is provided at the positive output of the operational amplifier 304. The first comparison signal $V_{min}$ corresponds to an offset signal generated at the comparison electrode 302 free of signaling material. The signal $V_{max}$ is based on the full signal generated on account of the signaling material 602 at the additional comparison electrode 603.

Another partial region of the evaluation circuit 601 is shown in the right-hand part in accordance with FIG. 6 and serves for the processing of the signal of the sensor electrode 301. A sensor signal of the sensor electrode 301 is fed to an inverting input of the comparator 402, whereas the noninverting input of the comparator 402 is coupled to the ground terminal 312. Furthermore, the sensor electrode 301 is coupled to a first terminal of a fourth capacitance 604 and to a first terminal of the switching element 403, the second terminals of the switching element 403 and of the fourth capacitance 604 being coupled to the output of the comparator 402 and to a signal output of the evaluation circuit 601, at which $V_{signal}$ is provided, that is to say the sensor signal of the sensor electrode 301.

Consequently, FIG. 6 shows an embodiment of the sensor assembly according to an example embodiment the invention which uses not just one comparison signal for the comparison with the measurement signal $V_{signal}$, but rather two comparison signals, namely $V_{min}$ and $V_{max}$. Particularly in the analysis of biomolecules such as DNA or proteins, for example it is advantageous to work with two such check positions, one of which supplies a full signal ($V_{max}$) and the other of which supplies only the background or zero signal $V_{min}$. The measurement signal is referred to the signal intensity of these two reference signals $V_{max}$, $V_{min}$. The embodiment of the pixel circuit 601 according to the invention supplies these three signals $V_{min}$, $V_{max}$ and $V_{signal}$ simultaneously. The measurement result $V_{signal}$ can therefore be compared directly with the comparison signals $V_{min}$ and $V_{max}$.

A description is given below, referring to FIG. 7, of a sensor arrangement 700 in accordance with a fifth example embodiment of the invention.

The sensor arrangement 700 is in turn provided with an evaluation circuit 701 divided into two partial regions in accordance with FIG. 7, namely into a first partial region for the processing of signals of the comparison electrode 302 and of the additional comparison electrode 602, and into a second partial region for the evaluation of the signals of the sensor electrode 301 and of a supplementary additional sensor electrode 702.

The evaluation of the comparison signals of the comparison electrode 302 and of the additional comparison electrode 602 is realized in the evaluation circuit 701 in exactly the same way as in the evaluation circuit 601 from FIG. 6.

DNA single strands 703 are immobilized as catcher molecules on the additional sensor electrode 702, which are different from the DNA single strands 311 on the first sensor electrode 301. In other words, the DNA single strands 703 can hybridize with particles to be detected having a sequence that is different than the sequence of particles to be detected which can hybridize with the catcher molecules 311.

The evaluation of the signals of the sensor electrode 301 and of the additional sensor electrode 702 is effected in exactly the same way as the evaluation of the comparison signals of the comparison electrode 302 and of the additional comparison electrode 602. The sensor signal at the negative output of the operational amplifier 304, which can be attributed to sensor events at the additional sensor electrode 702, is designated as $V_{signal1}$. The sensor signal at the positive output of the operational amplifier 304, which can be attributed to sensor events at the sensor electrode 301, is designated as $V_{signal2}$.

The sensor arrangement 700 constitutes a further development of the embodiment from FIG. 6. In accordance with FIG. 7, two measurement signals are related to two comparison signals. Consequently, it emerges from FIG. 7 that the number of reference signals and the number of measurement signals which can be evaluated within a sensor pixel 700 may be greater than 1.

Figure 8:
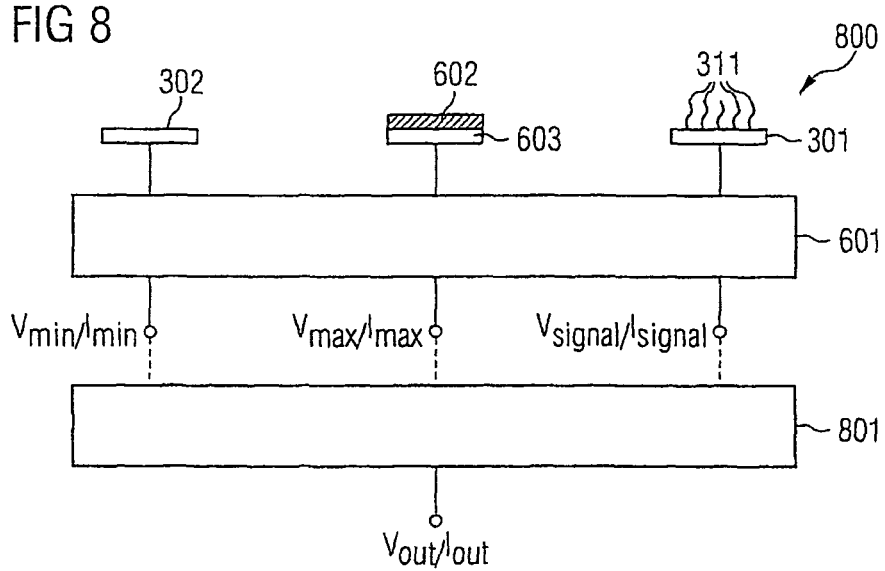
FIG. 8 shows a schematic view of a sensor assembly in accordance with one example embodiment of the invention.

A description is given below, referring to FIG. 8, of a sensor arrangement 800 in accordance with one example embodiment of the invention.

The sensor arrangement 800 represents a schematic view. A first voltage comparison signal $V_{min}$ (or a corresponding current signal $I_{min}$) is generated at the comparison electrode 302 and processed by means of the evaluation circuit 601. A full voltage signal $V_{max}$ (or a corresponding current signal $I_{max}$) is generated at the additional comparison electrode 603 provided with a signaling layer 602, which signal is processed by the evaluation circuit 601. A hybridization event between catcher molecules 311 on a sensor electrode 301 and particles to be detected gives rise to a sensor signal at the sensor electrode 301, which signal is evaluated by the evaluation circuit 601 and is provided as voltage signal $V_{signal}$ (or as current signal $I_{signal}$).

The evaluation circuit 601 is preferably provided within the sensor assembly 800, a further processing of the signals (in particular difference formation or analog/digital conversion) being realized by way of a signal further processing circuit 801. A voltage output signal $V_{out}$ (or a corresponding current signal $I_{out}$) is provided at an output of the signal further processing circuit, which signal is free of background signals and represents a direct measure of the sensor events at the sensor electrode 301.

To put it another way, the sensor assembly 800 represents a generalized form of the device according to an example embodiment of the invention. One important aspect is a circuit block 601 which is monolithically integrated in the sensor pixel and which evaluates the signals of the electrodes 302, 603, 301 and relates them to one another in a suitable form.

The sensor may be a planar electrode and may also have a finger structure, as is often the case in a redox cycling detection method. Transducers for the detection of biomaterial according to the impedance method can also be used there. It is possible to use any transducer which supplies a signal that can be evaluated and processed electrically. Said signal may be either an electrical voltage or else an electric current. The output signal of the evaluation block 801 may likewise be an electric current or an electrical voltage.

It should be noted that in the example embodiments described with reference to FIG. 3 to FIG. 8 it was assumed that the electrodes remain at a constant electrical potential during an experiment and the voltage jump is accomplished by an electrolyte. Consequently, all the sensors of a sensor assembly simultaneously measure and store a measurement result in the integration capacitances. As an alternative, it is also possible for each sensor to be addressed individually, so that the sensor electrode then carries out a voltage jump, whereas the electrolyte remains at a constant potential. Mixed forms in which both the electrolyte potential and the sensor electrode voltage change are also possible.

The electrode 302 used in FIG. 3 to FIG. 7 may optionally be free of a coating with catcher molecules, but may also be provided with a layer made of catcher molecules that are not ready for binding. What is crucial in accordance with this configuration is that no sensor event takes place on the electrode 302.

A description is given below, referring to FIG. 9, of an analog/digital converter 900 for forming a digital sensor signal from an analog sensor signal.

The full signal comparison signal $V_{max}$ is provided at a first reference potential terminal 901, and the zero signal comparison signal $V_{min}$ is provided at a second reference potential terminal 902. The sensor signal $V_{signal}$ is provided at an analog signal terminal 903. A multiplicity of nonreactive resistors 905, at which the voltage $V_{max}$-$V_{min}$ is dropped progressively, are provided between the first reference potential terminal 901 and the second reference potential terminal 902. A plurality of comparators 906 (comparator cascade) are furthermore provided, the sensor signal $V_{signal}$ being provided at a noninverting input of each comparator 906. The inverting input 909 of each of the comparators 906 is provided with a terminal arranged between two adjacent resistors 105.

Consequently, the signal $V_{signal}$ is provided at all the noninverting inputs of the comparators 906, and at the other inputs of the comparators 906 the signal drops progressively from $V_{max}$ to $V_{min}$. At the outputs of the comparators 906, a binary signal having a logic value "1" or "0", so-called thermometer code, is provided on the basis of the comparisons of the two signals at the inputs 908, 909. This thermometer code is converted into a binary signal by means of a thermometer-binary converter 907, that is to say into a digital signal, which is provided at the digital signal terminal 904.

Figure 9:
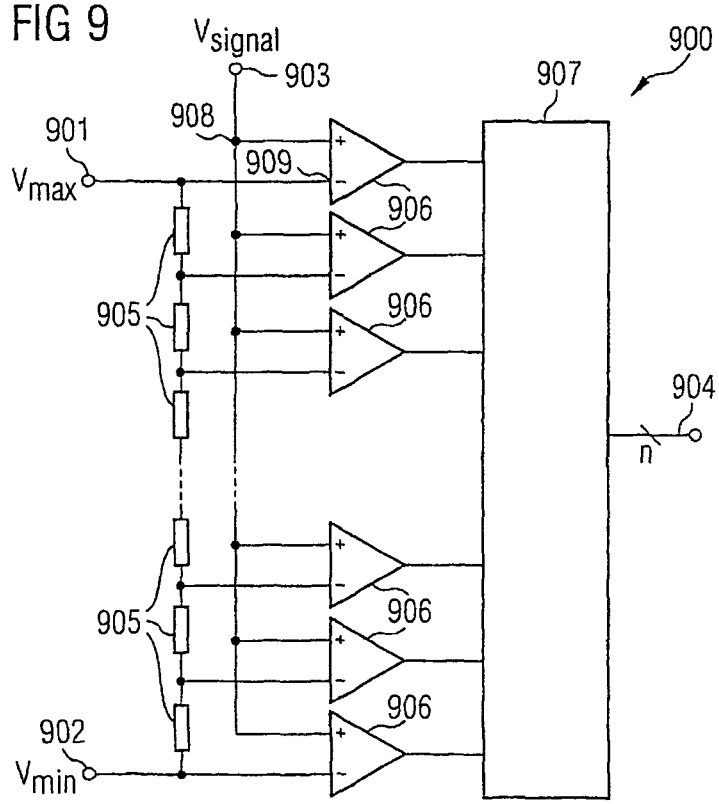
FIG. 9 shows an analog/digital converter of a sensor assembly according to an example embodiment of the invention.

To put it another way, FIG. 9 shows an embodiment of an analog/digital converter 900, which can be connected directly to the circuit devices 300 to 800 presented previously. If the voltage signals for the maximum value, the minimum value and the measured value are present, then the ADC 900 automatically outputs a digital word corresponding directly to the relative measurement signal.

The pixel circuits described below are in each case arranged below a sensor electrode and monolithically integrated into the silicon material, with the result that the respective circuit components described below are formed and connected up to one another, with the result that the functionalities described below are ensured.

The sensor arrangements described below are set up as DNA sensors for the detection of macromolecular biopolymers, an electrochemical method being used for detecting the macromolecular biopolymers in accordance with these example embodiments of the invention, which method involves effecting an indirect detection of a hybridization event by way of electrochemical markings on signal oligomers or catcher molecules or target molecules or intercalators. Intercalators are in particular substances which intercalate selectively at or in double-stranded DNA. This permits discrimination between single strands and double strands.

In accordance with the method described in [7], short-chain signal oligomers are hybridized with the catcher molecules (probe molecules) immobilized on the working electrodes. Afterward, the substance to be analyzed is brought into contact with the electronic chip and target molecules that are complementary to the respective probe molecules, also referred to as catcher molecules, in terms of their sequence and are possibly present in the substance to be analyzed displace the short-chain signal oligomers. Ferrocene molecules are usually attached as a marking to the signal oligomers. The electrochemical system subsequently detects the presence of the ferrocene molecules at the different sensor positions.

It should be noted in this context that the sensor assemblies described are suitable for all types of electrochemical experiments which involve carrying out an oxidation and/or a reduction of constituents of the electrolyte or of substances immobilized on the electrode surface.

The following embodiments thus describe a DNA analysis system for chronoamperometry and chronocoulometry which is generally able to realize a voltage jump of several 100 mV (typically 400 mV) within a time period of less than one microsecond, but in principle also arbitrarily longer time periods, at the respective working electrode.

Owing to the time requirements described above, the use of a macroscopic potentiostat circuit is not possible precisely for very small electrode areas, that is to say for electrodes having a very small surface area, since wiring capacitances and apparatus capacitances do not permit the required signal bandwidth. Since the operating circuits are arranged directly beneath the electrode in a pixel in the case of the DNA analysis system according to an embodiment of the invention as described below, the parasitic capacitance which the working electrode has to drive is considerably reduced and it is possible to achieve very short jump times.

Short jump times are necessary since, in this case, it is easily possible to distinguish between electrochemically active substances present directly on the electrode and diffusive contributions to the oxidation current or to the reduction current. The substances present directly on the respective electrode are oxidized or reduced within an extremely short time, while the free substances present in the analyte contribute to the signal current significantly later on account of their specific diffusion constants.

In a voltage jump experiment, the current at the working electrodes is essentially divided into three contributions:

Charge Reversal of the Double-Layer Capacitance:
The double-layer capacitance must always be taken into account if a conductive electrode is in contact with an electrolyte. In direct proximity to the electrode surface, ions are arranged in essentially two layers. This layer system can be interpreted as an (electrolytic) capacitor in which the two capacitor plates are just a few molecules away from one another. Owing to this fact, the (electrolytic) capacitor has extremely high values for the capacitance per unit area. Values of 0.1 $F/m^2$ are typically achieved.

With regard to the DNA sensor according to the invention it is apparent that the quantity of charge which flows into the double-layer capacitance is of the same order of magnitude as the quantity of charge applied for oxidation of the ferrocene.

Oxidation of the Ferrocene:
The ferrocene present on the electrode surface is directly oxidized during an effectively positive voltage jump at the working electrode. Since the hybridized molecules are only at most a few nanometers away from the surface, the oxidation of said molecules is effected almost completely within the jump time of the voltage. From a metrological standpoint, this current contribution is therefore superposed directly with the charging current of the double-layer capacitance.

Oxidation of Diffusing Ferrocene Molecules:

The analyte contains an appreciable concentration of ferrocene molecules, inter alia those which have been displaced by the catcher molecules. These molecules diffuse from the solution to the electrode and lead to an electric current flow which decays slowly after the step-function voltage change.

The primary measurement signal in this case is the current which flows at the electrode during the voltage jump. The metrologically relevant variable, however, is the quantity of charge required for stabilizing the electrode voltage. The quantity of charge is a direct measure of the absolute quantity of ferrocene which has been oxidized. An integrator is preferably provided in the sensor assembly for this case, which integrator integrates the respective electrode current.

Figure 10:
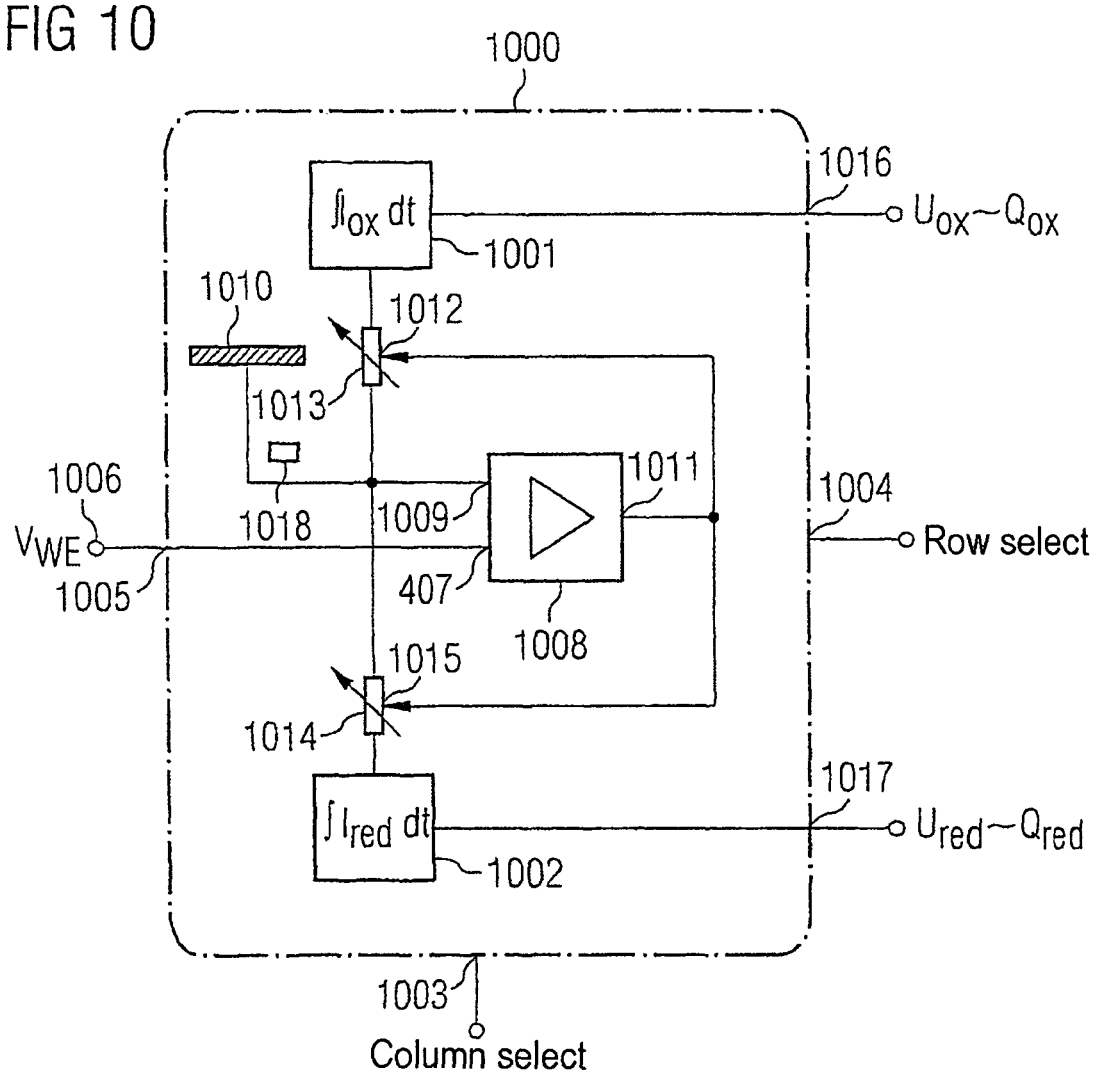
FIG. 10 shows a pixel circuit in accordance with one aspect of an example embodiment of the invention.

As is shown in the pixel circuit 1000 in FIG. 10, the respective integrator 1001, 1002 is contained directly in a respective sensor pixel. The pixel circuits described below are in each case to be understood such that each pixel circuit is arranged locally beneath or in direct proximity to a respective working electrode and is electrically coupled to the latter, for the detection of sensor events that in each case occur at the working electrode.

The pixel circuit 1000 in accordance with FIG. 10 has three inputs 1003, 1004, 1005 and also two outputs 1016, 1017 in addition to an oxidation integrator 1001 and a reduction integrator 1002.

A first input 1003, also referred to as the column select input, is coupled to a first column control unit. The column select signal is fed to the pixel circuit 1000 via the column select input 1003.

A second input 1004, also referred to as a row select input 1004, is coupled to a row control unit and serves for feeding the row select signal to the pixel circuit 1000.

Furthermore, a third input 1005 is provided for feeding a reference potential $V_{WE}$ 1006 to a first input 1007 of an operational amplifier 1008, which is likewise provided in the pixel circuit 1000. The second input 1009 of the operational amplifier 1008 is coupled to the working electrode 1010 of the respective pixel circuit 1000.

The output 1011 of the operational amplifier 1008 is coupled to a control input 1012 for varying an electrical resistance of a first regulatable electrical resistor 1013, one terminal of which is coupled to the input of the oxidation integrator 1001 and the other terminal of which is coupled to the second input 1009 of the operational amplifier 1008 and also to the working electrode 1010 and to a first terminal of a second regulatable resistor 1014, the second terminal of which is coupled to the input of the reduction integrator 1002. The control terminal 1015 of the second regulatable resistor 1014 is likewise coupled to the output 1011 of the operational amplifier 1008.

The output of the oxidation integrator 1001 is coupled to a first output 1016 of the pixel circuit 1000 and the output of the reduction integrator 1002 is coupled to a second output 1017 of the pixel circuit 1000. The electrode current 1018 flowing through the working electrode is integrated by means of the integrators 1001 or 1002. The resulting electrical voltage $U_{ox}$ at the output of the oxidation integrator 1001 or $U_{red}$ at the output of the reduction integrator 1002 is proportional to the respective oxidation charge quantity or reduction charge quantity as the metrologically relevant variable.

Figure 11:
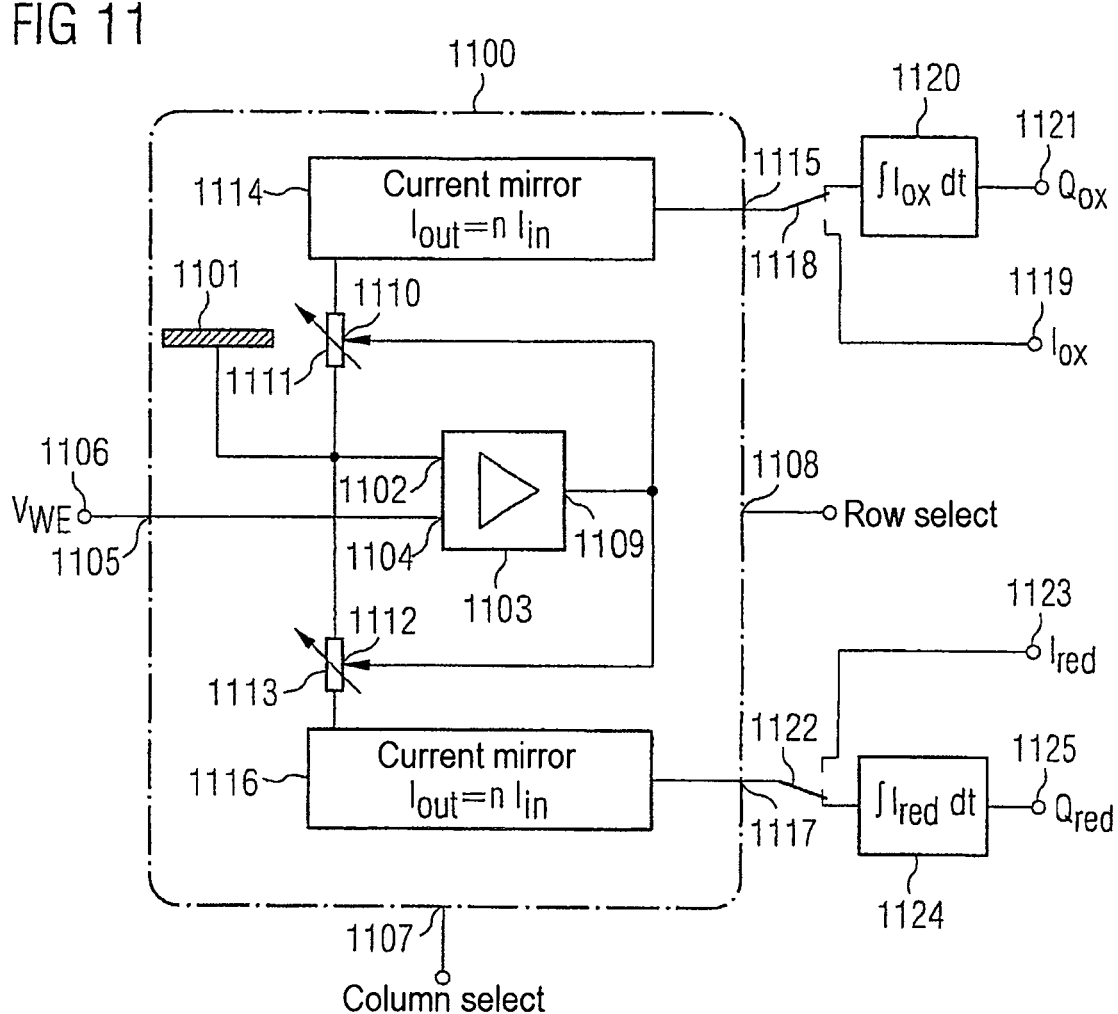
FIG. 11 shows a pixel circuit in accordance with another aspect of an example embodiment of the invention.

In accordance with an alternative configuration, the respective integrator is provided outside the pixel circuit, as shown for example in the pixel circuit 1100 in FIG. 11.

In the case of the pixel circuit 1100 in accordance with FIG. 11, too, the working electrode 1101 is coupled to a first input 1102 of an operational amplifier 1103, the second input 1104 of which is coupled to a third input 1105 of the pixel circuit 1100 for feeding in the reference potential $V_{WE}$ 1106.

The pixel circuit 1100 furthermore has a column select input 1107 and also a row select input 1108, the column select input 1107 being coupled to the column control unit and the row select input 1108 being coupled to the row control unit of a matrix-type array of pixel circuits.

The output 1109 of the operational amplifier 1103 is coupled to a control terminal 1110 of a first regularable resistor 1111 and also to a control terminal 1112 of a second regularable resistor 1113.

The first regularable resistor 1111 is coupled by its first terminal to an input of a first current mirror circuit 1114, the output of which is coupled to a first input 1115 of the pixel circuit 1100. The second terminal of the first regularable resistor 1111 is coupled to the working electrode 1101 and also to the second input 1102 of the operational amplifier 1103 and also to a first terminal of the second regularable resistor 1113, the second terminal of which is coupled to an input of a second current mirror circuit 1116, the output of which is in turn coupled to a second output 1117 of the pixel circuit 1100.

The electric current that flows through the working electrode 1101 and is amplified and multiplied by the current mirror parameter n by the first current mirror circuit 1114 is provided as amplified oxidation current at the first output 1115 and, depending on the switch position of a first switch 1118, is provided directly for further processing as first current output signal $I_{ox}$ 1119 or is fed to an oxidation integrator 1120, which forms the oxidation voltage $U_{ox}$ 1121 from the amplified oxidation current, the oxidation voltage being proportional to the oxidation charge quantity $Q_{ox}$.

An amplified reduction current is provided in a corresponding manner, multiplied by the factor n of the second current mirror circuit 1116, at the second output 1117 and, depending on the switch position of a second switch 1122, is provided directly as reduction output current $I_{red}$ 1123 or to a reduction integrator 1124, which provides a reduction output voltage $U_{red}$ 1125 proportional to the reduction charge quantity $Q_{red}$.

In this case, the respectively active selected sensor, that is to say the respective selected pixel circuit 1100, is connected to the respective central integrator (oxidation integrator 1120 or reduction integrator 1124) by means of a selection logic (represented by the symbolic switches 1118 and 1122 in FIG. 11) and the correspondingly flowing current is measured.

If the integrator is contained in the pixel circuit, as illustrated for example in the pixel circuit 1200 in FIG. 12, then the pixel circuits 1200 operate autonomously and, in principle, all the sensors of an array can be evaluated all at once.

The integrator results can be interrogated after the respective voltage jump experiment progressively by way of a suitable selection logic.

Figure 12 shows the pixel circuit 1000 in accordance with FIG. 10 in a simplified illustration, the illustration merely showing that the first input 1007 of the operational amplifier 1008 is coupled to the third input 1005 of the pixel circuit 1000 and the working electrode is coupled to the second input 1009 of the operational amplifier 1008.

A feedback capacitor 1201 is furthermore illustrated, the first terminal of which is coupled to the output 1011 of the operational amplifier 1008 and the second terminal of which is fed back to the second input 1009 of the operational amplifier 1008. A reset switch 1202 is connected in parallel with the feedback capacitor 1201 and coupled on the one hand to the second input 1009 of the operational amplifier 1008 and on the other hand to the output 1011 of the operational amplifier 1008, which is coupled to the output 1203 of the pixel circuit 1200 and at which the output voltage signal proportional to the quantity of charge is provided.

In particular, the working electrode circuit may be set up in such a way that it is possible to compensate for the quantity of charge from the double-layer capacitance that carries no information on account of a functionalization. In this case, the sensor array contains an electrode which is not functionalized, that is to say on which no catcher molecules are immobilized and which therefore measures exclusively the charge from the double-layer capacitance and the diffusive proportion.

The electric current which flows through this additional electrode during the voltage jump experiment or the integrated electrical charge can in each case be subtracted from the signals of the active sensors, so that these pixel circuits only supply the metrologically relevant charge signal or current signal.

FIG. 13A shows such an example embodiment, the pixel circuit being formed in accordance with the embodiment shown in FIG. 12.

As is illustrated in FIG. 13A, in accordance with this embodiment a reference circuit 1301 is provided having an input 1302, at which the reference potential $V_{WE}$ is provided. Furthermore, a reference working electrode 1303 is provided, on which no catcher molecules are immobilized or which is provided with a coating that is not ready for binding.

The input 1302 of the reference circuit 1301 is coupled to a first input 1304 of a reference operational amplifier 1305, the second input 1306 of which is coupled to the reference working electrode 1303. An output 1307 of the reference operational amplifier is fed back via a reference capacitor 1308 to the second input 1306 of the reference operational amplifier 1305 and, if appropriate, is short-circuited with the second input 1306 of the reference operational amplifier 1305 via a reference reset switch 1309 for resetting the integrator. An output 1310 of the reference circuit 1301 supplies the integrated reference signal $U_{ref}$ 1311. The difference between the output voltages of the two integrators, that is to say the difference between the output voltage provided by the pixel circuit 1200 and the reference output voltage provided at the output 1310 of the reference circuit is used as measurement signal for the electrochemical conversions at the working electrode 1010 of the respective pixel.

Figure 13B:
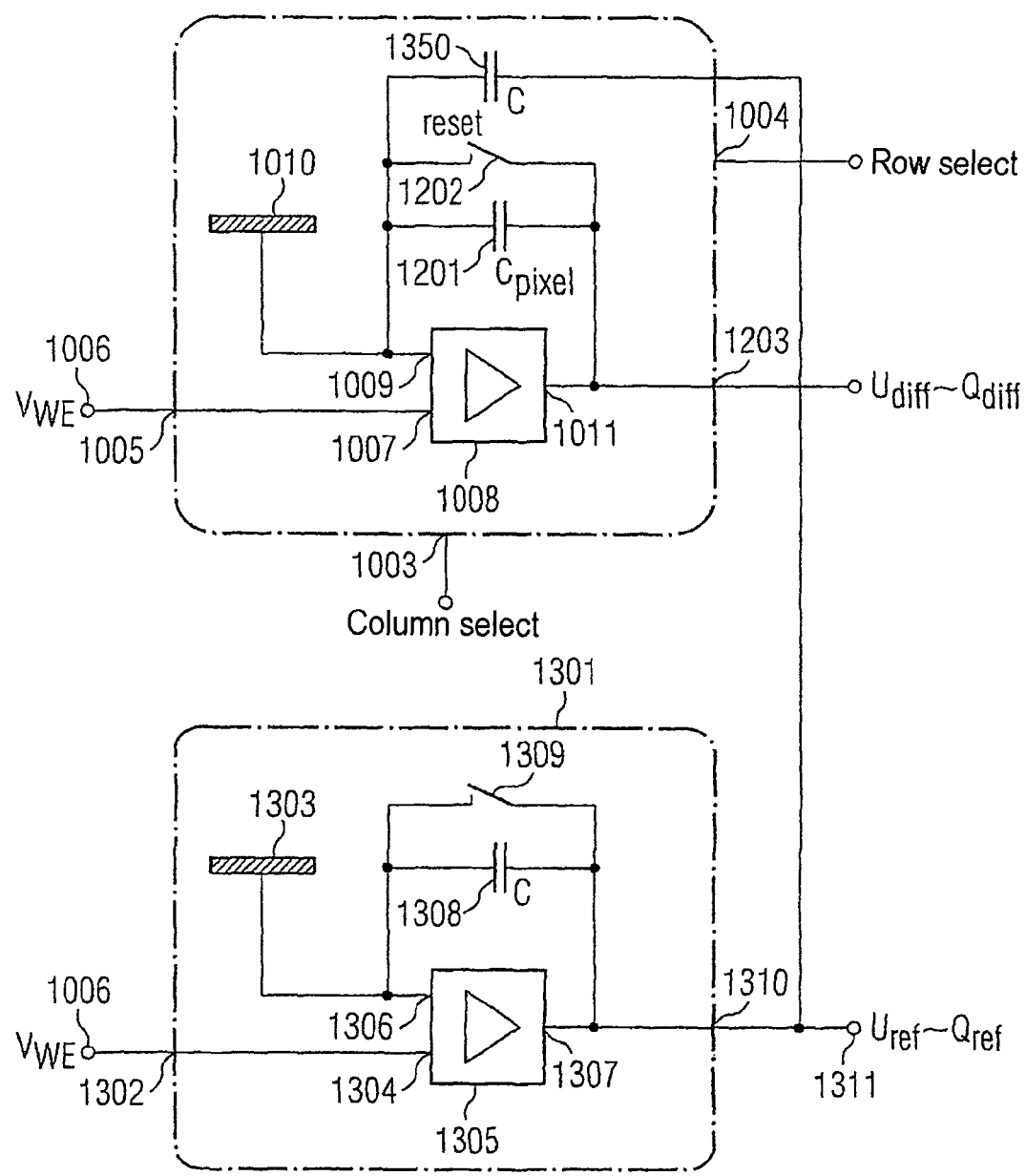

The embodiment shown in FIG. 13B differs from the embodiment shown in FIG. 13A by virtue of the fact that a central reference pixel is provided, which generates a central reference voltage signal $U_{ref}$ 1311, which is fed back to all the active sensor electrodes via a coupling capacitor 1350, and the double-layer capacitance and the diffusive conversions are exactly eliminated. The coupling capacitor 1350 is connected between the output of the central reference circuit 1301, which has the same construction as the reference circuit 1301 in accordance with FIG. 13A and is provided in each pixel, and the second input 1009 of the respective operational amplifier 1008 in the pixel circuit 1200.

The output signal of the respective pixel circuit 600 therefore directly outputs only the signal of the electrochemical conversions on account of the functionalization of the electrodes. This enables a very sensitive measurement of the quantities of charge occurring at the respective sensor, that is to say at the working electrode.

If the electrical charges originating from the oxidation processes or the reduction processes occur significantly later in time than the duration of the voltage jump, then it is possible to mask out the electrical charge carriers from the charging of the double-layer capacitance to the belated activation of the integrator.

The respective integrator is therefore only switched on in this case or enabled if the voltage at the working electrode or at the working electrodes has reached the target value and the metrologically relevant electrochemical conversions are effected.

The operating circuit of the working electrodes has the task of keeping the electrode potential constant and of measuring the current flowing through the working electrodes and/or the charge in the case of an oxidative voltage current and/or reductive voltage current. For this purpose, a differential stage is provided in the pixel circuit, which differential stage compares the electrode potential with the desired potential and measures the current necessary for holding the electrical voltage and/or stores the quantity of charge. Since the electric current can assume very large/small values in the case of large/small electrodes on account of the rapid voltage jump, it is expedient to amplify or divide the electrode current prior to further processing by means of current mirror circuits in such a way that the current assumes, for the integrated CMOS circuit technology that is preferably used, customary values which can be processed further by way of customary digital circuits.

The current mirrors described in the embodiments therefore have the division factor/gain factor n. The output current of the current mirror circuits is therefore n times the input current of the current mirror circuits. n may be less than 1 (for example ¹⁄₁₀₀, ¹⁄₁₀ for comparatively large electrodes) or greater than 1 (10, 100 for comparatively small electrodes).

For measuring oxidative signals and reductive signals, two complementary current paths are necessary which can take up and supply the respective electrode current, as shown for example in the pixel circuit 1100 in FIG. 11.

Figure 14:
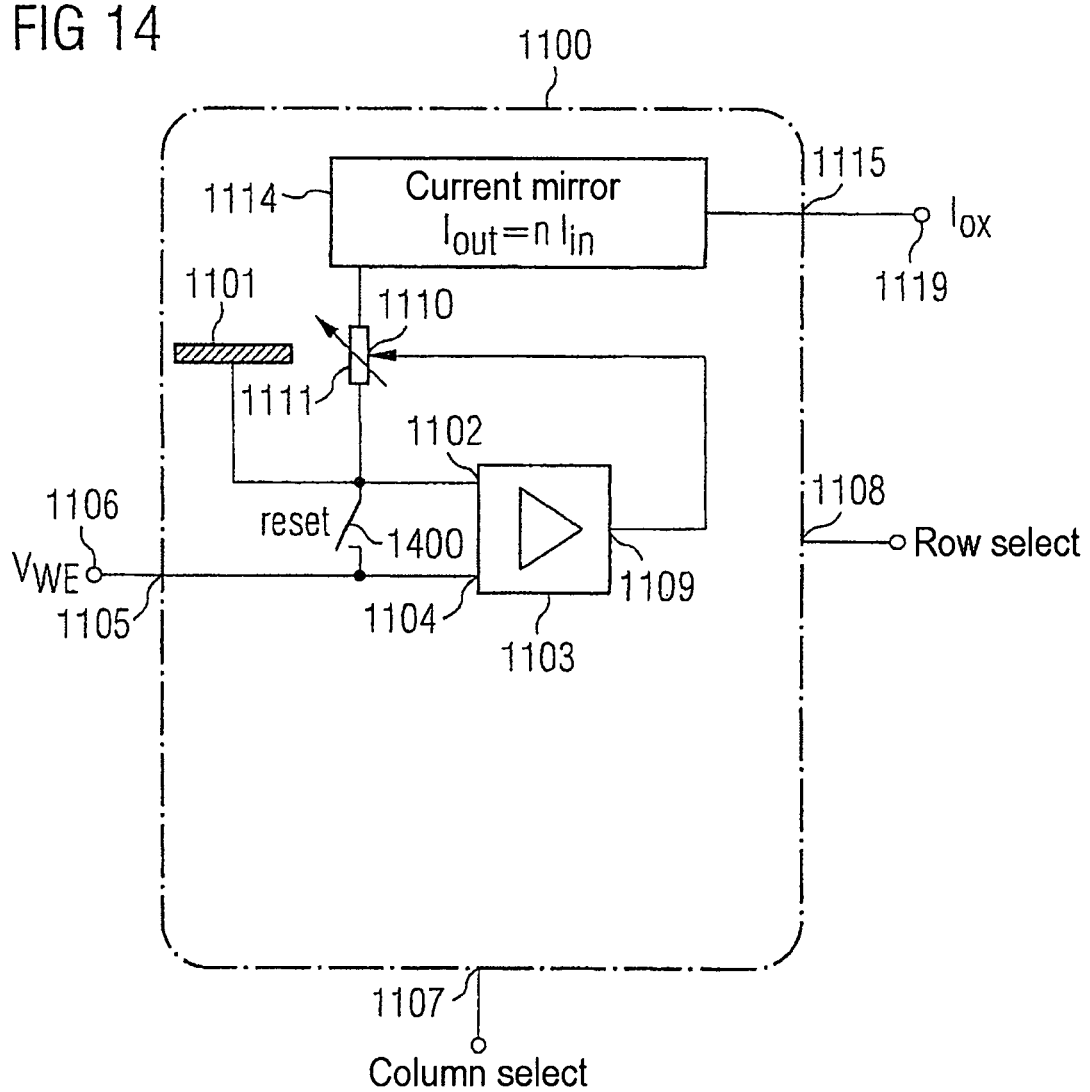
FIG. 14 shows a pixel circuit in accordance with another aspect of an example embodiment of the invention.

Usually, however, only one of the two electrochemical signals (oxidation/reduction) is metrologically relevant, which is why only one branch is provided, shown in a simplified illustration for example in FIG. 12. For simplification and miniaturization of the pixel circuits, therefore, one of the current branches in a pixel circuit may be embodied by a simple switch 1400 (cf. FIG. 14) which, prior to the actual measurement, connects the working electrode 1101 to the desired potential, that is to say the third input 1105 of the pixel circuit 1100 and conducts away to this voltage source an electric current possibly flowing.

It is furthermore desirable for the operating circuit of the working electrodes to have a very high dynamic range for the electrode current.

During the voltage jump, very large electric currents occur momentarily (double-layer capacitance, oxidation signal). Both this large pulse current and the subsequent small current from further oxidation processes have to be measured correctly by the operating circuit of the working electrodes.

Very precise current mirror circuits are desirable for this reason. A high accuracy of the current mirror circuits can be achieved by way of large-area current mirror circuits in order that process-technologically dictated statistical fluctuations of the component parameters of the current mirror circuits do not exceed a specific value. Since large-area transistors that form a current mirror circuit also have a large parasitic capacitance, the accuracy of a current mirror circuit integrated in the pixel circuit would be limited since said capacitance must likewise be charged by the electrode current. The quantity of charge does not appear or only appears very late at the output of the current mirror circuit and is therefore not available for the integration.

For a high accuracy and measuring speed it is expedient to precharge the current mirror units in the sensor pixel circuit prior to the voltage jump. This can be effected by way of a switching transistor 1501 of a precharge unit 1500 (cf. FIG. 15) coupled to the first current mirror circuit 1114, the switching transistor 1401 impressing the suitable current into the first current mirror circuit 1114 and being switched off again shortly before the voltage jump.

Figure 15:
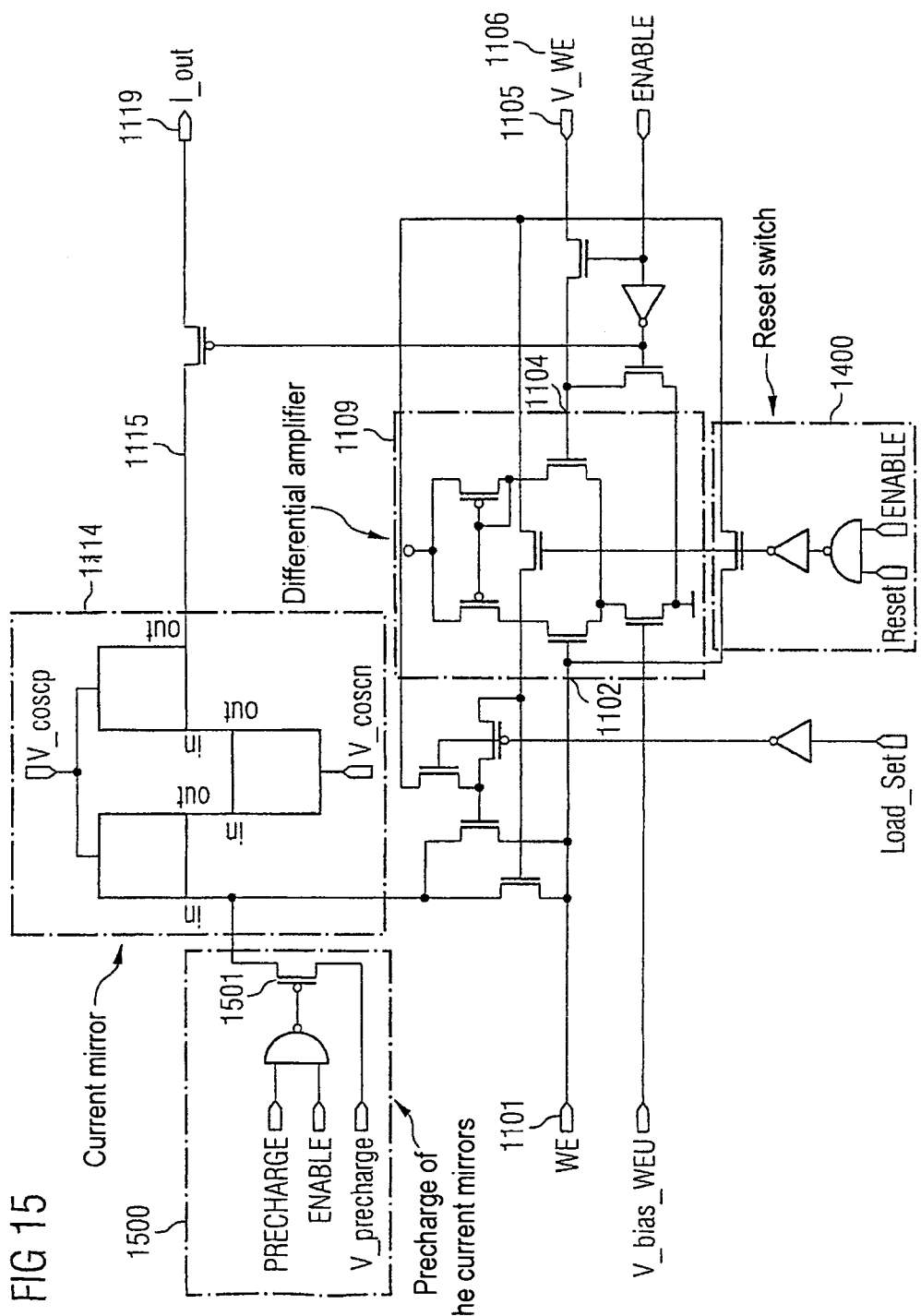
FIG. 15 shows a circuitry realization of an operating circuit with a precharge circuit for precharging the current mirrors.

In an optional embodiment, as illustrated in FIG. 15, additional switching elements may be provided, which are advantageous for setting the edge steepness.

Figure 16:
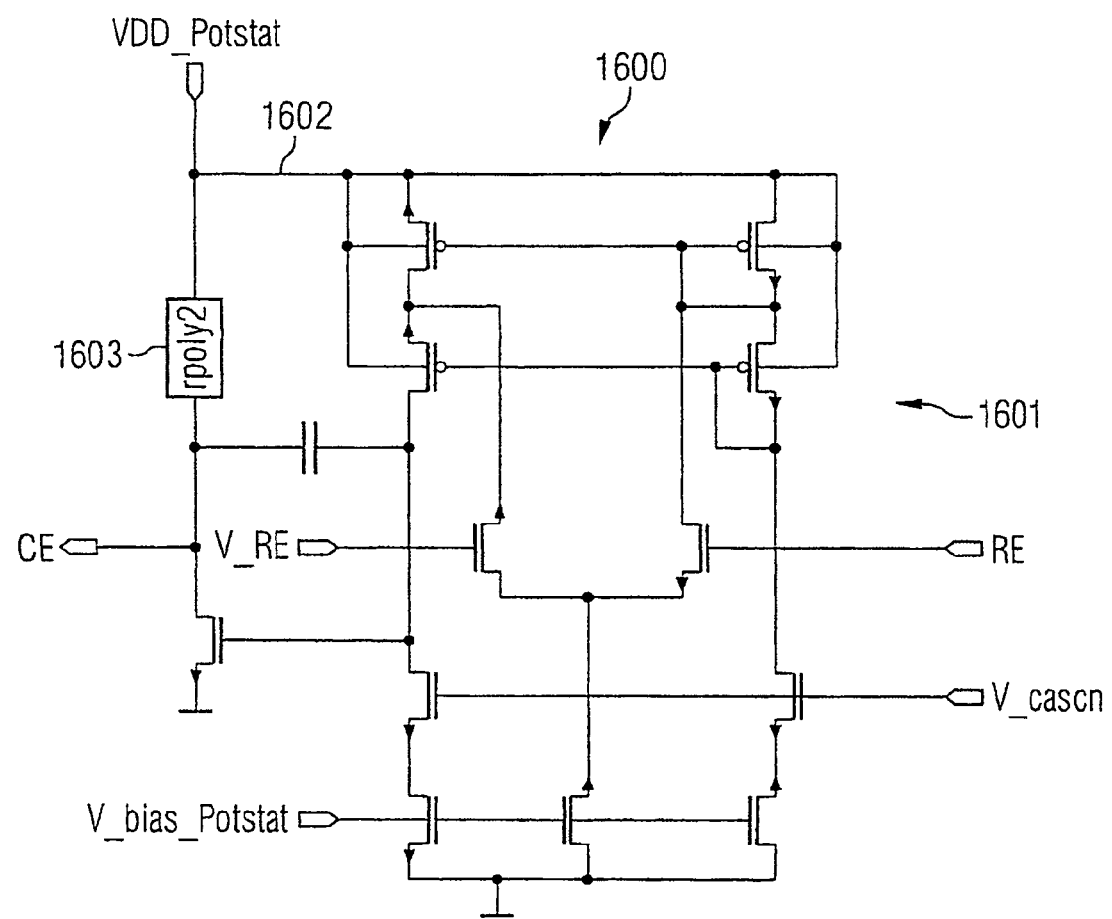
FIG. 16 shows a circuitry realization of the potentiostat circuit in accordance with one aspect of an example embodiment of the invention.

The potentiostat circuit 1600 illustrated in FIG. 16 serves for monitoring the electrolyte potential.

For this purpose, a reference electrode is fitted in the reaction volume, which reference electrode measures the electrolyte potential, compares it with a reference voltage and sets it in a suitable manner by way of a large-area counterelectrode of the electrolyte potential.

Since the potentiostat circuit 1600 has to change the potential of the electrolyte discontinuously in measuring methods according to an example embodiment of the invention, said circuit has a high signal bandwidth and also a high current driving capability according to an example embodiment of the invention.

Since the electrochemical system reference electrode/electrolyte/counterelectrode has complex electrical properties that are additionally dependent on the constituents of the electrolyte, it is necessary for the potentiostat circuit 1600 to be embodied such that it is very stable electrically in order to avoid oscillations.

This has been achieved in accordance with this configuration of the aspect of the invention through the use of a two-stage operational amplifier 1601 having an unreactive resistor 1603 in the positive output branch 1602. Although on the one hand this reduces the gain of the operational amplifier 1601, it nevertheless permits stable operation up to high frequencies with at the same time high output currents for capacitive loads.

In order to achieve a steep edge during the voltage jump, the analog jump voltage is not provided from outside the electronic chip, rather the two electrical potentials are present as a stable DC voltage signal at the electronic chip. After a trigger pulse, the input voltage at the potentiostat circuit 1600 is changed over between the two DC voltage signal values. The changeover can be effected very rapidly and merely requires a TTL signal (Transistor-Transistor Logic Signal).

If the sensors according to an example embodiment of the invention are arranged in an array, then the individual sensors are addressed by means of row lines and column lines. Consequently, the individual sensors can be selectively driven and/or read.

All interconnections of the sensor pixels such as are known per se for example in connection with redox cycling sensors can be used in connection with the measurement principles described above.

For the case where no integrator is provided in a respective sensor pixel, the electric current which is measured and conditioned in the active pixel is conducted via row lines or column lines to the edge of the sensor array and there after further signal processing it can be conducted in analog signal form or in digital signal form from the electronic chip or be integrated in analog fashion or digitally.

The sensor array is read progressively in this way. Since an individual measurement only requires a time of the order of magnitude of 1 ms, the entire sensor array can be read comparatively quickly. In particular, a plurality of sensor pixels can be activated simultaneously if the corresponding number of comparators is present.

Preferably, an entire column or row is activated and the sensor signal is detected at the edge of the matrix. In the case of all inactive sensor pixels, the electrode is deenergized or its voltage with respect to the electrolyte potential is chosen in such a way that no undesirable electrochemical conversions take place at the electrode.

If an integrator is in each case contained in the sensor pixels, then in principle all the sensor pixels can be activated simultaneously and, in a subsequent time interval, the integration results can be interrogated progressively by way of select lines from the individual pixels.

Situated in the periphery of the sensor matrix are further electronic circuits for the electrochemical operation of the sensor such as, for example, the potentiostat circuits and also evaluation circuits for the analog measurement signals and/or digital measurement signals, for example analog/digital converters, and furthermore digital circuits and analog circuits for driving the sensor array.

Completely digital communication between the electrochemical analysis system, i.e. sensor assembly, according to an example embodiment of the invention and a peripheral reader is particularly advantageous.

In this case, in particular, in addition an analog/digital converter for converting the analog measurement signal into a digital data signal and also a digital/analog converter for generating the required electrode voltage are provided in the sensor assembly and monolithically integrated in the latter. Furthermore, in this case provision is made of a computing unit for digital communication with the reader and also a communication interface at the sensor assembly for bidirectional data communication with the reader.

FIG. 17 shows a circuitry realization of the pixel circuit 1200 in accordance with FIG. 12.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The following publications are cited in this document:

[1] Hofmann, F. et al. "Passive DNA Sensor with Gold Electrodes Fabricated in a CMOS Backend Process" Proc. ESSDERC 2002, Digest of Tech. Papers, pages 487 to 490.

[2] Thewes, R. et al. "Sensor Arrays for Fully Electronic DNA Detection on CMOS", ISSCC, Digist of Tech. Papers, 2002, pages 350 to 351.

[3] Hintsche, R. et al. "Microelectrode arrays and application to biosensing devices", Biosensors & Bioelectronics, vol. 9, pages 697 to 705, 1994.
[4] Hintsche, R. et al. "Microbiosensors Using Electrodes Made in Si-Technology", Frontiers in Biosensorics, Fundamental Aspects, F. W. Scheller et al. (eds.), Dirk Hauser Verlag, Basel, pages 267 to 283, 1997.
[5] Paeschke, M. et al., "Voltametric Multichannel Measurements Using Silicon Fabricated Microelectrode Arrays", Electroanalysis, 1996, vol. 7, No. 1, pages 1-8.
[6] Obtainable on the Internet on Mar. 31, 2004 under the URL address: http://www.combimatrix.com
[7] Obtainable on the Internet on Mar. 31, 2004 under the URL address: http://www.frizbiochem.com
[8] DE 100 58 397 A1
[9] WO 03/046209 A2
[10] WO 02/097413 A2
[11] US 2004/0072223 A1
[12] A. J. Bard, L. R. Faulkner, "Electrochemical Methods. Fundamentals and Applications", John Wiley & Sons, 1980, page 559.
[13] U. Tietze, Ch. Schenk, "Halbleiterschaltungstechnik" ["Semiconductor circuitry"], Springer Verlag Berlin, 11th edition, 1999, pp. 954-955.
[14] M. Schienle et al., "A Fully Electronic DNA Sensor with 128 positions and In-pixel A/D Conversion", 2004 IEEE International Solid-State Circuits Conference (IEEE Cat. No. 04CH37519), IEEE Piscataway, N.J., USA, vol. 1, February 2004 (2004-02), pages 220-524, XP002352039 ISBN: 0-7803-8267-6.

List of Reference Symbols

100 Redox cycling sensor assembly
101 First gold working electrode
102 Second gold working electrode
103 Substrate
104 DNA catcher molecules
105 Analyte
106 First DNA single strands
107 Second DNA single strands
108 Redox-active marking
109 Additional molecules
110 Reduced molecules
111 Oxidized molecules
200 Interdigital electrode arrangement
201 Generator electrode
202 Collector electrode
203 Reference electrode
204 Counterelectrode
205 Substrate
206 Comparator
207 First ammeter
208 Second ammeter
300 Sensor assembly
301 Sensor electrode
302 Comparison electrode
303 Evaluation circuit
304 Operational amplifier
305 First capacitance
306 Second capacitance
307 First switching element
308 Second switching element
309 Third switching element
310 Fourth switching element
311 DNA single strands
312 Ground terminal
400 Sensor assembly
401 First comparator
402 Second comparator
403 Fifth switching element
404 Sixth switching element
405 Seventh switching element
406 Evaluation circuit
407 Third capacitance
500 Sensor arrangement
501 Evaluation circuit
502 Operational amplifier
600 Sensor assembly
601 Evaluation circuit
602 Signaling layer
603 Additional comparison electrode
604 Fourth capacitance
700 Sensor assembly
701 Evaluation circuit
702 Additional sensor electrode
703 DNA single strands
800 Sensor assembly
801 Signal further processing circuit
900 Analog/digital converter
901 First reference potential terminal
902 Second reference potential terminal
903 Analog signal terminal
904 Digital signal terminal
905 Resistors
906 Comparators
907 Thermometer-binary converter
908 First comparator input
909 Second comparator input
1000 Alternative pixel circuit
1001 Oxidation integrator
1002 Reduction integrator
1003 First input
1004 Second input
1005 Third input
1006 Reference potential $V_{WE}$
1007 First input of an operational amplifier
1008 Operational amplifier
1009 Second input of an operational amplifier
1010 working electrode
1011 Output of an operational amplifier
1012 Control input
1013 First regulatable electrical resistor
1014 Second regulatable electrical resistor
1015 Control terminal
1016 First output
1017 Second output
1018 Electrode current flowing through the working electrode
1100 Alternative pixel circuit
1101 Working electrode
1102 First input of an operational amplifier
1103 Operational amplifier
1104 Second input of an operational amplifier
1105 Third input of the pixel circuit
1106 Reference potential $V_{WE}$
1107 Column select input
1108 Row select input
1109 Output of an operational amplifier
1110 Control terminal
1111 First regularable resistor
1112 Control terminal
1113 Second regularable resistor
1114 First current mirror circuit 1115 First output of the pixel circuit
1116 Second current mirror circuit
1117 Second output of the pixel circuit
1118 First switch
1119 First current output signal $I_{ox}$
1120 Oxidation integrator
1121 Oxidation voltage $U_{ox}$
1122 Second switch
1123 Reduction output current $I_{red}$
1124 Reduction integrator
1125 Reduction output voltage $U_{red}$
1200 Alternative pixel circuit
1201 Feedback capacitor
1202 Reset switch
1203 Output of the pixel circuit
1300 Alternative pixel circuit
1301 Reference circuit
1302 Input
1303 Reference working electrode
1304 First input of a reference operational amplifier
1305 Reference operational amplifier
1306 Second input of a reference operational amplifier
1307 Output of a reference operational amplifier
1308 Reference capacitor
1309 Reference reset switch
1310 Output of the reference circuit
1311 Integrated reference signal $U_{ref}$
1350 Coupling capacitor
1400 Simple switch
1500 Precharge unit
1501 Switching transistor
1600 Potentiostat circuit
1601 Two-stage operational amplifier
1602 Positive output branch
1603 Nonreactive resistor

The invention claimed is:

1. A monolithically integrated sensor assembly configured for detecting DNA single strands possibly contained in an analyte, comprising:
   a substrate;
   at least one sensor electrode arranged at least one of on and in the substrate, and coated with a sensor-active layer at which are generated electrochemically active catcher DNA single strands in the presence of the DNA single strands to be detected, the electrochemically active catcher DNA single strands being detectable by producing an electrical sensor signal based on DNA single strands detected by the at least one sensor electrode;
   a plurality of comparison electrodes, at which a plurality of electrical comparison signals independent of the electrical sensor signal is detected, wherein the plurality of comparison electrodes is configured for measuring the electrical comparison signal simultaneously with measurement of the electrical sensor signal detected by the at least one sensor electrode in the presence of the DNA single strands to be detected, and the electrical comparison signal is at least one selected from a background signal, a noise signal and a zero signal which do not originate from the sensor event; and
   an operating circuit integrated at least one of on and in the substrate, and configured for driving the at least one sensor electrode, the operating circuit including at least one evaluation unit,
   wherein said evaluation unit is configured to carry out a statistical averaging of the comparison signals detected from the plurality of comparison electrodes and to jointly evaluate the sensor signal and the statistical averaging of the comparison signals so as to eliminate undesirable disturbing contributions whereby detection sensitivity is increased, signal-to-noise ratio improved, and noise margin increased.

2. The monolithically integrated sensor assembly as claimed in claim 1, wherein the substrate is a CMOS chip.

3. The monolithically integrated sensor assembly as claimed in claim 1, wherein the monolithically integrated sensor assembly is at least one of a biosensor assembly and a chemosensor assembly.

4. The monolithically integrated sensor assembly as claimed in claim 1, wherein the at least one evaluation unit is configured for determining a difference between the electrical sensor signal and the statistical averaging of the electrical comparison signal.

5. The monolithically integrated sensor assembly as claimed in claim 1, wherein the at least one evaluation unit includes an operational amplifier, integrated in the substrate, and configured for processing both the electrical sensor signal and the electrical comparison signals.

6. The monolithically integrated sensor assembly as claimed in claim 5, wherein the operational amplifier is configured for integrating electrical charge carriers.

7. The monolithically integrated sensor assembly as claimed in claim 1, wherein at least one of the comparison electrodes is free of a sensor-active layer.

8. The monolithically integrated sensor assembly as claimed in claim 1, wherein at least one of the comparison electrodes includes a signaling coating configured for generating a determined quantity of the electrochemically active particles in the case of a determined change in an electrical potential, independently of the sensor event.

9. The monolithically integrated sensor assembly as claimed in claim 1, wherein the at least one sensor electrode and the plurality of comparison electrodes have an essentially identical geometry.

10. The monolithically integrated sensor assembly as claimed in claim 1, further comprising:
   means for keeping constant electrical potentials at the at least one sensor electrode and at the plurality of comparison electrode.

11. The monolithically integrated sensor assembly as claimed in claim 10, wherein the means for keeping constant the electrical potentials includes at least one capacitance.

12. The monolithically integrated sensor assembly as claimed in claim 1, further comprising:
   a subtraction capacitance configured to form the difference between the electrical sensor signal and the electrical comparison signal, a first terminal of the subtraction capacitance being coupled to the at least one sensor electrode, and a second terminal of the subtraction capacitance being coupled to the plurality of comparison electrode.

13. The monolithically integrated sensor assembly as claimed in claim 1, further comprising:
   a first comparison electrode at which a zero signal is generated;
   a second comparison electrode at which a full signal is generated.

14. The monolithically integrated sensor assembly as claimed in claim 1, further comprising:
   an analog/digital converter configured for determining a digital output signal based on the electrical sensor signal and the plurality of electrical comparison signals.

15. The monolithically integrated sensor assembly as claimed in claim 13, further comprising:
an analog/digital converter configured for determining a digital output signal based on the electrical sensor signal and the electrical comparison signals, wherein the zero signal and the full signal form an upper and a lower electrical reference potential of the analog/digital converter.

16. A sensor array, comprising a plurality of monolithically integrated sensor assemblies, each of which is formed at least one of on and in a substrate, each of the monolithically integrated sensor assemblies comprising:
at least one sensor electrode arranged at least one of on and in the substrate, and coated with a sensor-active layer at which are generated electrochemically active catcher DNA single strands in the presence of the DNA single strands to be detected, the electrochemically active catcher DNA single strands being detectable by producing an electrical sensor signal based on DNA single strands detected by the at least one sensor electrode; and
a plurality of comparison electrodes, at which a plurality of electrical comparison signals independent of the electrical sensor signal are detected, wherein the plurality of comparison electrodes is configured for measuring the electrical comparison signal simultaneously with measurement of the electrical sensor signal detected by the at least one sensor electrode in the presence of the DNA single strands to be detected, and the electrical comparison signal is at least one selected from a background signal, a noise signal and a zero signal which do not originate from the sensor event.

17. The sensor array as claimed in claim 16, wherein at least one of the comparison electrodes is provided jointly for at least one portion of the monolithically integrated sensor assemblies.

18. The sensor array as claimed in claim 16, further comprising:
a drive unit configured for selectively driving one of the monolithically integrated sensor assemblies, a portion of the monolithically integrated sensor assemblies or all of the monolithically integrated sensor assemblies.

19. A method for producing a monolithically integrated sensor assembly configured for detecting DNA single strands possibly contained in an analyte, the method comprising:
forming, at least one of on and in a substrate, at least one sensor electrode coated with a sensor-active layer at which are generated electrochemically active catcher DNA single strands in the presence of the DNA single strands contained in the analyte to be detected, the electrochemically active catcher DNA single strands being detectable by producing an electrical sensor signal detected by the at least one sensor electrode;
forming at plurality of comparison electrode for producing a plurality of comparison signals from exposure to the analyte simultaneously with the electrical sensor signal detected by the at least one sensor electrode in the presence of the DNA single strands to be detected, the plurality of electrical comparison signals being at least one selected from a background signal, a noise signal and a zero signal which do not originate from the sensor event; and
integrating an operating circuit, configured for driving the at least one sensor electrode, the operating circuit including at least one evaluation unit by which a sensor event is determined at the at least one sensor electrode based on the electrical sensor signal and the plurality of electrical comparison signal,
wherein the comparison electrode lacks the sensor-active layer provided on the sensor electrode,
wherein the operating circuit is operative for producing statistical averaging of the plurality of the electrical comparison signals and a difference signal from the signals of the measuring electrode and the statistical averaging as a measurement signal which is free of undesirable disturbing contributions based on charge reversals of double-layer capacitances at the electrode surfaces.

20. The sensor array as claimed in claim 17, further comprising:
a drive unit configured for setting up to selectively drive one of the monolithically integrated sensor assemblies, a portion of the monolithically integrated sensor assemblies or all of the monolithically integrated sensor assemblies.

21. The monolithically integrated sensor assembly as claimed in claim 1, further comprising at least one additional electrode coated with a sensor-active layer at which are generated other electrochemically active catcher DNA single strands in the presence of other DNA single strands to be detected that are different than the DNA single strands to be detected by the at least one sensor electrode, the other electrochemically active DNA single strands being detectable via detection of another electrical sensor signal at the at least one additional electrode.

22. The method as claimed in claim 19, further comprising at least one additional electrode coated with a sensor-active layer at which are generated other electrochemically active catcher DNA single strands in the presence of other DNA single strands to be detected that are different than the particles to be detected by the at least one sensor electrode, the other electrochemically active particles being detectable via detection of another electrical sensor signal at the at least one additional electrode.

23. The method as claimed in claim 19, further wherein the determined electrical potential is measured with respect to an electrolyte and the potentiostat circuit is autonomously operated so as to stabilize the electrical potential in the electrolyte at a reference potential.

24. The monolithically integrated sensor assembly as claimed in claim 1, wherein the operating circuit is adapted for autonomously operating the potentiostat circuit so as to stabilize the determined electrical potential measured in an electrolyte at a reference potential.

* * * * *